(12) United States Patent
Jennewein et al.

(10) Patent No.: US 11,834,691 B2
(45) Date of Patent: Dec. 5, 2023

(54) PROCESS FOR PURIFICATION OF A SIALIC ACID FROM A FERMENTATION BROTH

(71) Applicant: Chr. Hansen HMO GmbH, Rheinbreitbach (DE)

(72) Inventors: Stefan Jennewein, Bad Honnef (DE); Markus Helfrich, Bad Hoenningen (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 425 days.

(21) Appl. No.: 16/765,407

(22) PCT Filed: Oct. 31, 2018

(86) PCT No.: PCT/EP2018/079908
§ 371 (c)(1),
(2) Date: May 19, 2020

(87) PCT Pub. No.: WO2019/101489
PCT Pub. Date: May 31, 2019

(65) Prior Publication Data
US 2020/0332325 A1    Oct. 22, 2020

(30) Foreign Application Priority Data
Nov. 21, 2017 (EP) .................................. 17202833

(51) Int. Cl.
| | | |
|---|---|---|
| *C12P 19/02* | (2006.01) | |
| *C07H 1/06* | (2006.01) | |
| *C07H 7/027* | (2006.01) | |
| *A23L 33/125* | (2016.01) | |
| *A23L 33/00* | (2016.01) | |
| *A61K 31/7012* | (2006.01) | |
| *C12P 19/26* | (2006.01) | |
| *C07H 1/08* | (2006.01) | |
| *C07H 3/08* | (2006.01) | |

(52) U.S. Cl.
CPC ............. *C12P 19/02* (2013.01); *A23L 33/125* (2016.08); *A23L 33/40* (2016.08); *A61K 31/7012* (2013.01); *C07H 1/06* (2013.01); *C07H 1/08* (2013.01); *C07H 3/08* (2013.01); *C07H 7/027* (2013.01); *C12P 19/26* (2013.01)

(58) Field of Classification Search
CPC ............. C07H 1/06; C07H 7/027; C12P 19/02
See application file for complete search history.

(56) References Cited

U.S. PATENT DOCUMENTS

| | | |
|---|---|---|
| 5,679,645 A | 10/1997 | Ikeuchi et al. |
| 2003/0109007 A1 | 6/2003 | Koizumi et al. |
| 2010/0143535 A1 | 6/2010 | Motoshima et al. |
| 2015/0240277 A1* | 8/2015 | Jennewein ............... C12P 19/18 435/97 |
| 2016/0333042 A1* | 11/2016 | Jennewein ................. A61P 1/00 |
| 2020/0332331 A1* | 10/2020 | Jennewein ............ A23L 33/135 |

FOREIGN PATENT DOCUMENTS

| | | |
|---|---|---|
| CN | 104072533 A | 10/2014 |
| CN | 104628794 A | 5/2015 |
| CN | 106 929 461 A | 7/2017 |
| DE | 39 37 891 A1 | 5/1991 |
| EP | 0 474 410 A2 | 3/1992 |
| EP | 0 578 825 A1 | 1/1994 |
| EP | 1 484 406 A1 | 12/2004 |
| EP | 2 258 216 A1 | 12/2010 |
| JP | H02261343 A | 10/1990 |
| JP | H08119986 A | 5/1996 |
| JP | 2010505403 A | 2/2010 |
| JP | 2017506065 A | 3/2017 |
| WO | 94/29476 A1 | 12/1994 |
| WO | 2008/040717 A2 | 4/2008 |
| WO | 2008/097366 A2 | 8/2008 |
| WO | 2009008362 A1 | 1/2009 |
| WO | 2012/083329 A1 | 6/2012 |
| WO | 2015/071401 A1 | 5/2015 |
| WO | 2015106943 A1 | 7/2015 |
| WO | 2016/091265 A1 | 6/2016 |

OTHER PUBLICATIONS

Lewatit(R) S 2568 Product Information, Edition: Oct. 23, 2020, pp. 1-5; also available at https://lanxess.com/en/Products-and-Solutions/Products/I/LEWATIT—S-2568 (Year: 2020).*
PCT International Search Report for PCT/EP2018/079908, dated Feb. 11, 2019.
WPI Week 201570 Thomson Scientific, London, GB; AN 2015-440430 XP002781294, & CN 104 628 794 A (Wuhan Zhongke Guanggu Green Biological) May 20, 2015 (May 20, 2015) abstract.
Database WPI Week 199629 Thomson Scientific. London. GB; AN 1996-283501 XP002781295, & JP HOS 119986 A (Nissin Shokuhin Kaisha Ltd) May 14, 1996 (May 14, 1996) cited in the application abstract.
Wang, et al., "Sialic Acid Is an Essential Nutrient for Brain Development and Cognition," Annu. Rev. Nutr., (2009), vol. 29, No. 1: 177-222.
Varki, et al., "Diversity in cell surface sialic acid presentations: implications for biology and disease," Lab. Invest., (2007), vol. 87: 851-857.
Comb, et al., "The Sialic Acids, The Structure and Enzymatic Synthesis N-acetylneuraminic acid", J. Biol. Chem., (1960), vol. 235: 2529-2537.

* cited by examiner

*Primary Examiner* — Bahar Craigo
(74) *Attorney, Agent, or Firm* — McNeill Baur PLLC

(57) ABSTRACT

The present invention describes an efficient way to isolate a sialic acid from a fermentation broth. The sialic acid contained in the fermentation broth is produced by bacterial fermentation. The inventive process comprises a step of removing biomass from the fermentation broth, a step of subjecting the resulting solution to at least one of a cationic ion exchanger treatment and an anionic ion exchanger treatment and a step of removing salts after the ion exchanger treatment. The process can provide the sialic acid in spray-dried form as well as in form of sialic acid crystals.

34 Claims, 8 Drawing Sheets

PROCESS FOR PURIFICATION OF A SIALIC ACID FROM A FERMENTATION BROTH

CROSS-REFERENCE TO RELATED APPLICATIONS

This application is the National Stage entry of International Application No. PCT/EP2018/079908, filed 31 Oct. 2018, which claims priority to European Patent Application No. 17202833.4, filed 21 Nov. 2017.

BACKGROUND

Field

The present invention describes an efficient way to isolate a sialic acid from a fermentation broth. The sialic acid contained in the fermentation broth is produced by bacterial fermentation. The inventive process comprises a step of removing biomass from the fermentation broth, a step of subjecting the resulting solution to at least one of a cationic ion exchanger treatment and an anionic ion exchanger treatment and a step of removing salts after the ion exchanger treatment. The process can provide the sialic acid in spray-dried form as well as in form of sialic acid crystals.

Description of Related Art

Sialic acid is a generic term for the N- or O-substituted derivatives of neuraminic acid, a monosaccharide with a nine-carbon backbone and possessing a carboxylic acid function. The carboxylic acid group can confer to the sugar at an appropriate pH a negative charge. All known sialic acid structures are derived from four primary core structures (a) 2-Keto-3-deoxynononic acid (Kdn), (b) neuraminic acid (Neu), (c) N-acetylneuraminic acid (Neu5Ac) and (d) N-glycolylneuraminic acid (Neu5Gc), with potential substitutions at the hydroxyl groups on C-4, C-7, C-8, and C-9 (O-acetyl, O-methyl, O-sulfate, O-lactyl or phosphate groups). Lactones may occur between C-2 and C-7, C-4, or C-8, or a lactam between C-2 and the C-5 amino group of Neu. In addition, also naturally occurring dehydro sialic acids are known, like 2-deoxy-2,3-didehydro-N-acetylneuraminic acid (Neu2en5Ac, also known as DANA). Dehydro sialic acids like DANA can possess inhibitory properties towards sialidases and thus potential inhibitory properties against certain viruses (e.g. influenza virus).

A sialic acid usually exist as α-glycoside which occupies the non-reductive terminal of hetero-oligosaccharides in glycol-conjugates, such as glycolipids and glycoproteins, and provide an extreme example of glycan diversity, both in structure and function. The family of sialic acids consist of more than 40 derivatives of the nine-carbon neuraminic acid, including N- and O-substituted ones. The structural features of the members of said family are specialized due to the amino group at position 5 and the carboxyl group at position 1, which make all sialic acids strong organic acids with a negative charge under physiological conditions.

Sialic acids are present as the terminal saccharides of the glycans present in cell-surface glycoconjugates (glycoproteins and glycolipids) in vertebrates and higher invertebrates. Sialic acids are also components of the lipopolysaccharides and capsular polysaccharides of pathogenic bacteria including *Escherichia coli* K1, *Haemophilus influenzae*, *Haemophilus ducreyi*, *Pasteurella multo-cida*, *Neisseria gonorrhoeae*, *Neisseria meningitidis*, *Campylobacter jejuni* and *Streptococcus agalactiae*. In mammals, sialic acids are found primarily as the terminal residue of sugar conjugates on the cell surface. Two derivatives of Neu are the most common sialic acid structures found on mammalian cells: N-acetylneuraminic acid (Neu5Ac) and its hydroxylated derivative, N-glycolylneuraminic acid (Neu5Gc). Among mammals, humans are a known exception in their lack of Neu5Gc, due to an inactivation mutation in a hydroxylase, which modifies CMP-Neu5Ac to CMP-Neu5Gc.

With no unsubstituted form of neuraminic acid found in nature, the most widely found sialic acid is N-acetylneuraminic acid (also abbreviated as "Neu5Ac" or as "NANA"). Neu5Ac is a sialic acid of which the N-atom of the amino group is acetylated. In the literature, the term "sialic acid" is sometimes used as a synonym for the specific sialic acid Neu5Ac, but in the following, the term "sialic acid" is understood as the family of all sialic acids and Neu5Ac is understood as a particular member of said family, namely N-acetylneuraminic acid.

Neu5Ac carries out various biological functions by acting as a receptor for microorganisms, viruses, toxins and hormones. Neu5Ac is a characteristic component of amino sugars that are important for cell-cell interactions.

Another significant naturally occurring variation is N-glycolylneuraminic acid (Neu5Gc), which is formed by substituting one of the hydrogen atoms in the methyl moiety of the acetyl group by a hydroxyl group. Neu5Gc exists in a large number in animal species, especially in porcine tissue, but has not been detected in human tissue except in individuals afflicted by particular types of cancer.

Among other things, Neu5Ac serves to protect proteins from degradation by proteases. Due to the high concentration of Neu5Ac in gangliosides, which occur in the membranes of nerve cells, Neu5Ac is attributed an important role in neuronal development, as well as in the function of the neuronal system. In addition, it is known that numerous viral pathogens, such as human influenza viruses or avian influenza viruses, utilize sialylated compounds in the infection of the human organism. Neu5Ac, compounds comprising Neu5Ac, and compounds derived from Neu5Ac are already being used in active substances against viral infections. Further research is focused on the use of these compounds to ensure optimal neuronal development or to prevent degenerative brain diseases.

Neu5Ac modification of cell surface molecules plays a role in many biological phenomena such as protein structure stability, regulation of cell adhesion, and signal transduction. Neu5Ac deficiency disorders such as GNE Myopathy, which is also known as Hereditary Inclusion Body Myopathy (HIBM), Distal Myopathy with Rimmed Vacuoles (DMRV) or Nonaka Myopathy, are clinical diseases resulting from a reduction in sialic acid production. The production of Neu5Ac is the key reason why the mutation causes the disease. Replacing a metabolite after the genetic block in the pathway could, in theory, alleviate symptoms of a Neu5Ac deficiency. (Jay et al., Gene Reg. and Sys., 2009 Biology 3:181-190). However, administering one or more compounds in the Neu5Ac biosynthetic pathway in vivo is a significant challenge. These compounds have extraordinarily rapid clearance rates and are excreted in the urine before they can be metabolized.

Inside the human body, the highest concentration of Neu5Ac could be found in the brain, where Neu5Ac participates as an integral part of the ganglioside structure in synaptogenesis and neural transmission (Wang et al., Eur. J. Clin. Nutr. 2003 November; 57(11):1351-69). Especially in the first year of life, Neu5Ac seems to play a major role in brain development. The rapid growth of infant brains places an exceptionally high demand on the supply of nutrients from the diet, particularly for preterm infants. Neu5Ac is an essential component of brain gangliosides and the polysialic acid (polySia) chains that modify neural cell adhesion molecules (NCAM). Sialic acid levels are high in human breast milk, predominately the levels of the specific sialic acid Neu5Ac. In contrast, infant formulas contain a low level of both Neu5Ac and Neu5Gc (Wang, Annu. Rev Nutr. 2009; 29:177-222). Therefore, Neu5Ac shows a high potential for use in infant formulas to support the development of the infant brain.

Sialic acids play important roles in many physiological and pathophysiological processes including the development of the embryonic nervous system, metastasis, the regulation of immune responses, and infections with bacteria or viruses. Sialic acids are an essential component of brain gangliosides and of the polysialic acid chains that modify neural cell adhesion molecules (NCAMs) that facilitate cell-to-cell interactions, neuronal outgrowth, the modification of synaptic connectivity and memory formation. In piglets, a diet rich in sialic acids increases the level of brain sialic acids and the expression of two learning-related genes. Accordingly, the diet also enhances learning and memory.

Infants, in particular pre-term infants, have a high demand for nutrients including sialic acids due to the rapid brain growth and the development of their immune system at this developmental stage. There are also high levels of sialic acids, particularly Neu5Ac, in human breast milk (~0.5 g/L). In contrast, infant formulas to date contain low or even negligible amounts of Neu5Ac. Besides free Neu5Ac, human milk contains various acidic, i.e. sialylated, oligosaccharides belonging to the family of human milk oligosaccharides (HMOs) (Urashima T. et al., (2011) Nutrition and diet research progress: Milk oligosaccharides, Nova Sciences Publishers Inc, New York, ISBN-978-1-61122-831-1), most notably 3'-sialyllactose, 6'-sialyllactose, and sialylated derivatives of lacto-N-tetraose (LNT) such as LST-a, LST-b, LST-c and disialylated-LNT. While milk from some mammals, like for example rodents, are particularly rich in sialylated milk oligosaccharides, human milk is particular rich in neutral oligosaccharides, such as 2'-fucosyllactose, 3-fucosyllactose, Lacto-N-tetraose, Lacto-N-neotetraose and Lacto-N-fucopentaose I.

Another aspect, which is important in drug development, is that active substances should have stable possible crystalline morphology for pharmaceutical quality medicinal formulations. Those skilled in the pharmaceutical arts understand that crystallization of an active pharmaceutical ingredient offers the best method for controlling important physiochemical qualities, such as stability, solubility, bioavailability, particle size, bulk density, flow properties, polymorphic content, and other properties. Thus, there is a need for crystalline forms of sialic acids like Neu5Ac and processes to produce such forms. These crystalline forms should be suitable for pharmaceutical use.

Another use for derivatives of Neu5Ac is the use as neuraminidase inhibitors for the treatment of viral infections, e.g. influenza. As one example, Neu5Ac is a potential raw material in the synthesis of Zanamivir, which can be used to prevent and treat the infections of both influenza types A and B, such as the avian influenza virus H5N1 (Kawei et al., Clin Infect Dis 2009, 48:996-997). Moreover, Neu5Ac has a broad range of medical applications, such as anti-cancer, anti-adhesion, and anti-inflammatory activities (Varki et al., Lab Invest 2007, 87:851-857).

The high cost of Neu5Ac is due to its scarce availability and supply. There are several strategies for preparing Neu5Ac. Traditionally, Neu5Ac is extracted from natural substances such like egg yolks, milk whey and edible bird nests.

However, the content of Neu5Ac in natural sources is relatively low, as a result of which the separation and purification processes are relatively complex, time-consuming and burdensome, particularly in view of the complicated purification process, impure starting material and a low yield (Tao et al., Appl Microbiol Biotechnol 2010, 87:1281-1289). Therefore, conventional methods are not cost-effective for large-scale production of Neu5Ac.

As described before, Neu5Ac could be isolated from edible bird nests. Edible bird nests are the natural resource with the highest content of Neu5Ac. The content of Neu5Ac in edible bird nests is up to 100 g/kg in contrast to 2 g/kg in egg yolk (Koketsu et al., Glycoconj J. 1992 April; 9(2):70-4.). In most cases, Neu5Ac is not completely purified, but only fortified. The product is then sold as Bird Nest Extract. This bird Nest Extract contains only 1.5% sialic acid (Bird's Nest Extract, ORYZA OIL & FAT CHEMICAL CO., LTD).

CN 104072533 A discloses a way to isolate Neu5Ac from a bird nest. The material will be incubated with water and heated up to 121° C. and freeze dried. Neu5Ac was removed from the so treated nest by adding ethanol. The ethanol was filtered to remove insoluble materials and incubated with ethyl acetate to precipitate Neu5Ac. This leads Neu5Ac with a purity of around 79% and a purification yield of 55 to 60%.

One possible way for industrial production of Neu5Ac is chemical synthesis. For example, N-Acetyl-glucosamine (GlcNAc) and oxaloacetate can be condensed under alkaline conditions, followed by decarboxylation (described by Cornforth et al., Biochem. J. 1958 68:57-61). Another way is the preparation by asymmetric synthesis from D-mannose and non-sugar precursors such as 1,2-cis-dihydro-catechol (Danishefsky et al., J. Am. Soc. 1988, 110:3929-3940). However, in most cases, the chemical synthesis of Neu5Ac contains or requires laborious repetitive sequential protection and deprotection steps and could led to the formation of a number of reaction intermediates and isomers. These facts could result in a highly complex, difficult and high-cost separation process.

The third option for an industrial production of Neu5Ac is production via biocatalytic processes. Said biocatalytic processes include enzymatic catalysis, whole-cell biocatalysis and fermentation. Biocatalysis and fermentation processes have emerged to an important tool to produce different substances. These techniques are used for the large-scale production or synthesis of bulk chemicals, agrochemical intermediates, active pharmaceuticals and food ingredients. Biocatalysis and fermentation offers the possibility for easy and low cost production of different substances. Most of the methods employ environment-friendly operations under mild conditions.

For the production of Neu5Ac, two different enzymes are described which can be used for the biocatalyic or enzyme-based production. The enzymes are Neu5Ac synthase (EC 4.1.3.19) and Neu5Ac aldolase (NAL, previously named Neu5Ac lyase, EC 4.1.3.3). Neu5Ac aldolase is preferred over the Neu5Ac synthase because its substrate pyruvate is much more available than the substrate phosphoenolpyruvate of the Neu5Ac synthase (Tao et al., Appl. Microbiol. Biotechnol. 2010, 87:1281-1289). NAL was first used for Neu5Ac production in 1960 with N-acetyl-D-mannosamine (ManNAc) and pyruvate as raw materials (Comb et al., J Biol Chem 160 235:2529-2537). One critical point for a large-scale production of Neu5Ac with this method is the cost of N-acetyl-D-mannosamine which is very high. Furthermore, N-acetyl-D-mannosamine is not available in large quantities to date.

DE 39 37 891 A1 discloses that the production of Neu5Ac with biocatalytic processes that can be transferred to a larger scale. The isomerization of N-acetylglucosamine catalyzed by the N-acetylglucosamine-2-eperimerase (EC5.1.3.8) to N-acetylmanosamine and a subsequent reaction in the presence of N-acetylneuraminic acid pyruvate lyase (EC4.1.3.3) and pyruvate to Neu5Ac can successfully be performed in a bioreactor.

WO 94/29476 A1 discloses an in vitro-method for the preparation of N-acetyl-D-neuraminic acid from N-acetyl-D-glucosamine (NAG, GlcNAc). In the preparation, NAG is converted to N-acetyl-D-mannosamine (NAM, ManNAc) by base-catalyzed epimerization. Subsequently, NAM reacts with pyruvate in a reaction catalyzed by Neu5Ac-aldolase to yield Neu5Ac. The Neu5Ac-aldolase was prepared from recombinant *E. coli*-cells expressing the said Neu5Ac-aldolase. The aldolase enzyme was immobilized by mixing Eupergit-C® beads with a crude extract of said recombinant *E. coli* cells. The conversion of NAM to Neu5Ac was initiated by adding the said immobilized enzyme beads to a mixture of NAM and pyruvate. Neu5Ac was obtained from the reaction mixture in that the enzyme was removed by filtration and the filtrate was mixed with glacial acetic acid and a small quantity of seed to obtain a "wet cake". The wet cake was subjected either to acetone desolvation or rhomboid crystallization.

EP 0 578 825 A1 discloses an in vitro-process for the production of Neu5Ac by treating a mixture of N-acetylglucosamine and pyruvic acid with an N-acetylneuraminic acid lyase under alkaline conditions. The reaction product was isolated by ion-exchange column chromatography using Dowex 1 (Dow Chemical Company), and isolates were concentrated by crystallization.

To avoid the use of N-acetyl-D-mannosamine for the reaction mixture, an enzymatic approach is known in which N-acetyl-D-glucosamine is used as substrate. During a first step N-acetyl-D-glucosamine was converted by the N-acyl-D-glucosamine-2-epimerase into N-acetyl-D-mannosamine with a conversion rate of 77%. During a second step, the so produced N-acetyl-D-mannosamine and pyruvate was used as substrates for the N-acetylneuraminic lyase to produce Neu5Ac (Maru et al., Carbohydrate Research, 1998; 306: 575-578). With this method it was possible to produce 29 kg of Neu5Ac from 27 kg of N-acetyl-D-glucosamine. The produced Neu5Ac was recovered by direct crystallization. The solution was heated for 5 min to 80° C. to precipitate the containing enzymes. The insoluble parts were removed by filtration. To recover the Neu5Ac from the reaction mix, 5 volumes of glacial acetic acid was added to the solution. After crystallization, the Neu5Ac was recovered by filtration and washed with ethanol to remove the remaining acetic acid. The material was dried at 40° C. until a constant weight was obtained. Using high performance liquid chromatography (HPLC) and infrared (IR) spectroscopy the so produced and isolated Neu5Ac were indistinguishable from natural Neu5Ac.

This method for production of Neu5Ac is also known from another approach for a large-scale production. In said approach, Neu5Ac is synthesized using an aldolase enzyme preparation [N-acetylneuraminate lyase; CAS: 9027-60-5; E.C.: 4.1.3.3. aldolase enzyme] obtained from a modified strain of an *Escherichia coli* K12-derivative. The enzyme catalyses the coupling of N-acetylmannosamine and sodium pyruvate to produce N-acetylneuraminic acid. (Gras Notice 602, GRAS Exemption Claim for N-Acetyl-D-neuraminic acid (NANA), Glycom A/S). The Neu5Ac produced in this way is then purified in several steps. The first step is to remove the proteins from the catalytically production step by filtration. After filtration, the anhydrous Neu5Ac is removed from the reaction mixture by crystallization. After the first crystallization step the material was solved again, treated with charcoal to remove color and impurities and crystallized again to receive the Neu5Ac in crystalline dihydrate form. However, biocatalytic production of sialic acid is only technical feasible at multi-hundred kg scale and not a realistic option for providing a sialic acid, such as Neu5Ac, at multi-ton scale for the application in food products, such as infant and toddler nutrition products. Including Neu5Ac at a natural concentration of approx. 0.5 g/l in a infant nutrition product would require an amount of about 3.75 g Neu5Ac per one kg of infant food formula. Thus, even for a "small" infant food formula product, several tons of material are the result. In addition, biocatalytic production of sialic acid is far too expensive for food application today.

In addition to the biocatalytic production method in vitro, there is also the possibility to produce Neu5Ac by fermentation with the help of microorganisms in vivo. In this case, the used enzymes will be produced inside the microorganism, but will not be isolated as described above. Rather, the whole cell is used as the reaction cup, Neu5Ac is produced inside the cells and during production, Neu5Ac is secreted into the surrounding media. After fermentation, Neu5Ac is isolated from the culture broth. For production of Neu5Ac, especially bacteria like *E. coli* and yeast are described in the literature.

EP 1 484 406 A1 describes a process for producing Neu5Ac using a microorganism which has the ability to produce Neu5Ac but has limited or no ability to decompose Neu5Ac compared with a wild-type strain, such that Neu5Ac accumulates in the culture medium and can be recovered therefrom. To enable the production of Neu5Ac, the microorganism possesses strong N-acetylneuraminic acid synthase activity and/or N-acetylglucosamine 2-epimerase activity. CN 106 929 461 A discloses a process for the production of Neu5Ac using *Bacillus subtilis* cells which expresses genes encoding for a glucosamine-fructose-6-phosphate transaminase, a glucosamine-6-phosphate N-acetyltransferase, a N-acetylglucosamine isomerase and a N-acetylneuraminic acid synthase. The cells further have the ptsG gene, which encodes a glucose-specific component of the phosphotransferase system EIICBA, deleted. A yield of 0.66 g·L-1 Neu5Ac was obtained by cultivating these cells in a glucose-containing medium.

Zhu, D. and colleagues (Zhu, D. et al. (2017) Biotechnol. Lett. 39: 227-234) report that using a high copy number co-expression vector for overexpression of PEP synthesis-related genes, pck and ppsA in *E. coli* enhance Neu5Ac production. More specifically, *E. coli* cells were subjected to random mutagenesis and a cell line that grew favourably on medium containing glucose but showed limited or no growth on medium containing Neu5Ac was transformed with an expression plasmid encoding N-acetylneuraminic acid synthase and N-acetylglucosamine-2-epimerase. After a period of cultivation, the cells were pelleted by centrifugation, stored at −20° C. as so-called "wet cells" and used as needed after thawing. For the production of Neu5Ac, a reaction mixture (30 mL) was provided comprising 90 g·L$^{-1}$ N-acetylglucosamine, 50 g·L$^{-1}$ glucose, 10 mL·L$^{-1}$ xylene and 200 g·L$^{-1}$ of said wet cells being permeabilized by the presence of 4 g·L$^{-1}$ detergent. After completion of the in-vitro reaction, the formation of Neu5Ac was evaluated by HPLC.

US 2003/0109007 A1 discloses a process for the production of Neu5Ac by utilizing permeabilized microorganisms. The method comprises the preparation of a mixture containing (i) a culture of a microorganism having N-acetylneuraminic acid aldolase activity or N-acetylneuraminic acid synthetase activity, or treated matter derived from the culture; (ii) a culture of a microorganism capable of producing pyruvic acid (or treated matter derived from the culture), or a culture of a microorganism capable of producing phosphoenolpyruvic acid (or treated matter derived from the culture); (iii) N-acetylmannosamine; and (iv) an energy source which is necessary for the formation of pyruvic acid or phosphoenolpyruvic acid. The mixture is prepared in an aqueous medium containing a chelating agent or surfactant allowing the formation and accumulation of Neu5Ac in the aqueous medium.

The reaction products were quantified using a carbohydrate analysis system. The drawbacks of the aforementioned processes are that only small-scale production is possible and (an excess of pyruvate is required to drive the reaction equilibrium towards Neu5Ac. In addition, N-acetylglucosamine, N-acetylmannosamine and phosphoenolpyruvate are expensive substrates for these reactions.

WO 2008/040717 A2 discloses a method for the production of Neu5Ac comprising the cultivation of a microorganism in a medium, wherein said microorganism carries heterologous genes encoding a sialic acid synthase (NeuB) and a UDP-GlcNAc epimerase (NeuC), wherein said microorganism is devoid of a gene encoding CMP-Neu5Ac synthase (NeuA) or wherein any genes encoding CMP-Neu5Ac synthase (NeuA) have been inactivated or deleted, and wherein endogenous genes coding for a sialic acid aldolase (NanA), for the sialic acid transporter (NanT) and, optionally, for ManNAc kinase (NanK) have been deleted or inactivated. Neu5Ac has been purified from the supernatant (2 liters) of a culture by precipitation using glacial acetic acid.

WO 2008/097366 A2 concerns metabolically engineered E. coli cells producing Neu5Ac. In said cells, the nanT (sialic acid transporter) and nanA (sialic acid aldolase) genes are inactivated, and the neuC and neuB genes that facilitate Neu5Ac biosynthesis in Neisseria meningitidis group B are introduced and overexpressed using expression plasmids in said nanT-nanA E. coli cells. In addition, the E. coli glucosamine synthase gene (glmS) is co-overexpressed with neuB and neuC. Neu5Ac was purified from the culture broth by ion-exchange chromatography.

CN 106929461 A concerns genetically engineered strain of Bacillus subtilis that improves the production of Neu5Ac. The amount of Neu5Ac in fermentation cultures was determined by HPLC. It was therefore an objective to provide microbial organisms that are capable of producing Neu5Ac more efficiently on an industrial scale, and with the use of an inexpensive carbon source as a sole carbon source.

WO 2012/083329 A1 discloses methods and agents for the production of Neu5Ac by genetically engineered fungal cells of the genus Trichoderma, which constitutively express N-acetylglucosamine-2-epimerase and N-acetylneuraminic acid synthase. Such Trichoderma cells were cultivated in the presence of GlcNAc. The mycelia of such Trichoderma stains were analyzed for the presence of Neu5Ac by HPLC-MS.

EP 0 474 410 A2 discloses a method for the production of Neu5Ac by hydrolyzing dilapidated egg yolk. The method comprises the steps of desalting a solution containing Neu5Ac obtainable by hydrolyzing delipidated egg yolk, adsorbing Neu5Ac to an anion-exchange resin and then eluting Neu5Ac. The desalting can be achieved by using a reverse osmosis membrane, an electrodialysis membrane or a dialysis membrane. The adsorbing process may comprise passing the desalted hydrolysate through a cation-exchange resin and further passing it through an anion-exchange resin. The final eluate was dried under reduced pressure to obtain a solid.

JP 08-119986 A describes a method for the purification of Neu5Ac or an analog thereof comprising the synthesis of Neu5Ac by condensing N-acetylmannosamine with pyruvic acid in the presence of sialic aldolase. The solution containing Neu5Ac or an analogue thereof is concentrated using an evaporator. The concentrated solution is mixed with an organic acid containing two or three carbon atoms. Subsequently, the mixture is heated to 50° C. and allowed to stand at 4° C. to precipitate white crystals of Neu5Ac.

The existing attempts to provide a purified sialic acid have only involved small-scale demonstrations, but no process for purification of a sialic acid to food-grade purity and food-grade quality from a fermentation broth in large scale is available to date.

SUMMARY

It was an object of the present invention to provide a process for a large-scale (industrial-scale) purification of a sialic acid (e.g. Neu5Ac) at a high degree of purity. Specifically, the process should be suitable for providing a sialic acid in kg-scale to tonne-scale in food-grade quality and should be suitable for being run in a continuous manner.

The object is solved by the process according to claim 1, the composition according to claim 19, the food composition according to claim 22, the liquid, ready-to-use infant or toddler nutrition product according to claim 29, the spray-dried infant formula product according to claim 30, the dietary supplement according to claim 31, the premix according to claim 32 and the use of the composition according to claim 34. The dependent claims illustrate advantageous embodiments.

According to the invention, a process for the purification of a sialic acid from a fermentation broth is provided. The process comprises the following steps:

removing biomass from a fermentation broth comprising a sialic acid, wherein a clarified solution is provided, providing a purified solution by subjecting the clarified solution to a cationic ion exchanger treatment with a cationic ion exchanger material, wherein the cationic ion exchanger treatment is performed under conditions in which the sialic acid passes the cationic ion exchanger material and is present in the flowthrough; and an anionic ion exchanger treatment with an anionic ion exchange material, wherein the anionic ion exchanger treatment is performed under conditions in which the sialic acid passes the anionic ion exchanger material and is present in the flowthrough; and removing salts from the purified solution by electrodialysis.

DETAILED DESCRIPTION OF A PREFERRED EMBODIMENT

Figure 1:
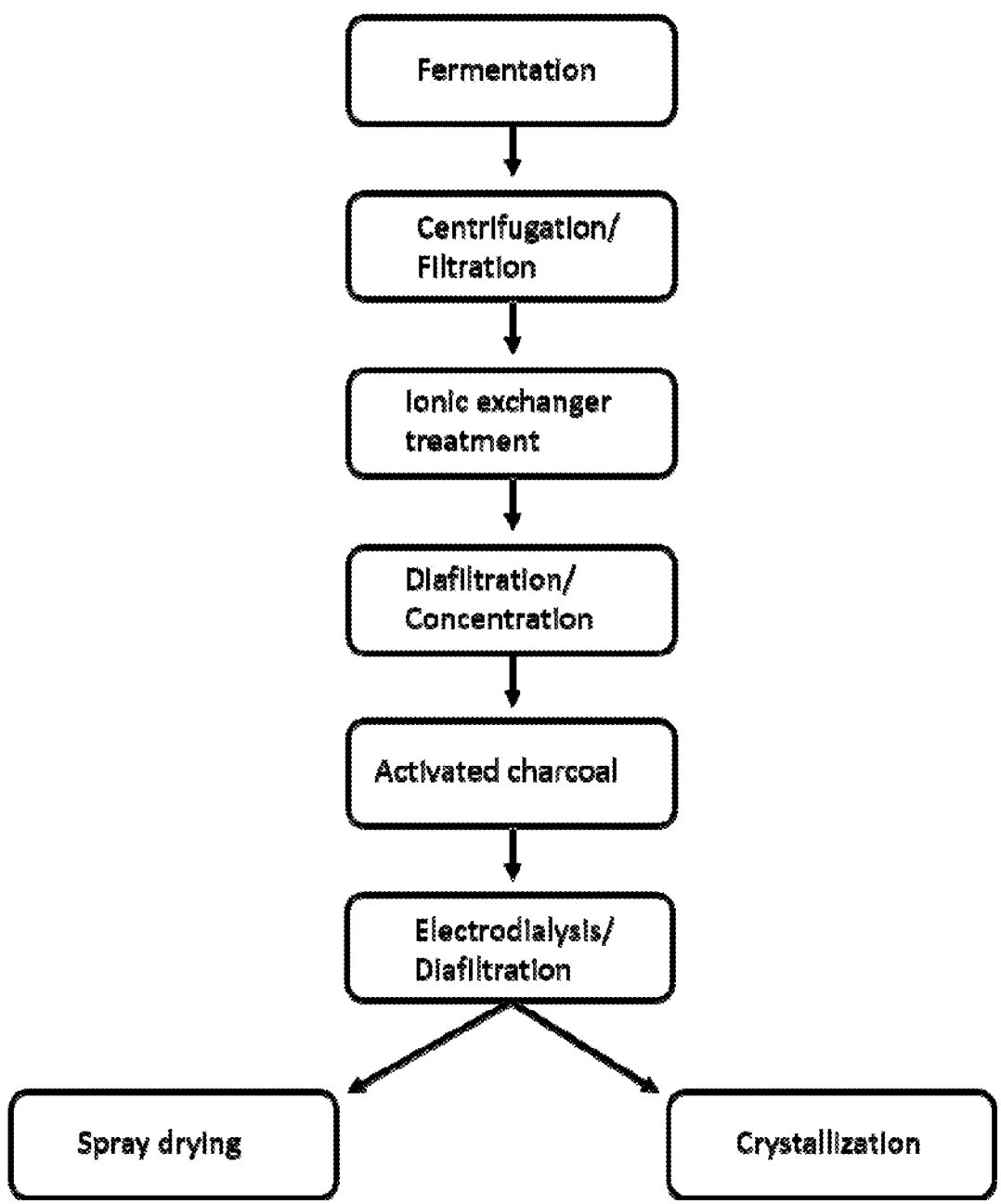
FIGS. 1-8 depict embodiments as described herein.

The inventive process is suitable for providing a desired sialic acid at a high degree of purity (food grade quality) and in large-scale (industrial-scale ranging from kg to tonnes per run). In addition, the inventive process can be carried out very fast and in an unexpensive manner. It can thus be run very economically. Furthermore, the process can be carried in a batch manner or in a continuous manner. The latter improves obtainable yield per time even further. At the end of the process, the purity of the sialic acid can be >80%, preferably >90%, more preferably >95%, most preferably at least 98%.

The presented process for purification of a sialic acid is also advantageous in that the preparation of the sialic acid is free of recombinant DNA and recombinant proteins derived from the recombinant microbial fermentation strains which are used for the production of the desired sialic acid.

Notwithstanding that the inventive process was conceived for the purification of a specific sialic acid (e.g. Neu5Ac) from a fermentation broth, said process may also be used for the purification of a specific sialic acid produced by an enzymatic reaction in vitro, a so-called in vitro biocatalysis reaction, or by using a permeabilized whole cell biocatalysis approach. It is understood that the purification of the sialic acid from the reaction mixture of an in vitro biocatalysis reaction does not require removal of biomass from the reaction mixture. The reaction mixture of an in vitro biocatalysis reaction thus corresponds to the clarified process stream.

Definitions

According to the invention, the term "purity" refers to chemical purity and specifies the degree to which a substance, like a specific single sialic acid is undiluted or unmixed with extraneous material. Hence, the chemical purity is an indicator of the relationship between a single substance and by-products/impurities. Chemical purity is expressed as a percentage (%) and is calculated using the following formula:

$$\text{Percent Purity} = \frac{\text{Mass of desired compound in sample}}{\text{Total mass of sample}}$$

In a composition comprising a sialic acid, the purity of the sialic acid can be determined by any suitable method known to the skilled artisan, for example by using HPLC. An appropriate detector can be a detector selected from the group consisting of an electrochemical detector, a refractive-index (RI) detector, a mass-spectrometer (MS), a diode-array-detector (DAD) and an NMR detector. For example, in HPLC, the ratio of the area underneath the peak representing the amount of a specific sialic acid (e.g. Neu5Ac) to the sum of areas underneath the peaks representing both the amount of the specific sialic acid and compounds different to the specific sialic acid in the same chromatogram. However, this implies that all impurities can be analysed by the chosen HPLC method. Otherwise, a mass-balance approach, i.e. an absolute quantification of the desired product (e.g. Neu5Ac) is necessary. In said approach, pure substances are used as a reference for quantification of the purity, which is then judged against the dry-matter obtained from the roduct (desired product plus all impurities). Said mass-balance approach can also be used for determining purity according to the invention.

In accordance with this invention, the term "a sialic acid" refers to a sialic acid within the family members of all sialic acids. Thus, according to the invention, the sialic acid to be purified is preferably a N- or O-substituted derivative of neuraminic acid, more preferably a N-substituted derivative of neuraminic acid, even more preferably N-acetylneuraminic acid (2-keto-5-acetamido-3,5-dideoxy-D-glycero-D-galactononulopyranos-1-onic acid, abbreviated as "Neu5Ac" or "NANA"), N-glycolylneuraminic acid (abbreviated as "Neu5Gc"), or 2-deoxy-2,3-didehydro-N-acetylneuraminic acid (abbreviated as "Neu2en5Ac" or "DANA"). In a particularly preferred embodiment of the invention, the sialic acid is N-acetylneuraminic acid ("Neu5Ac" or "NANA").

According to the invention, a "culture broth" refers to any liquid after fermentation which contains a sialic acid to be purified. The terms "culture broth", "fermentation broth" and "culture medium" are used as synonyms herein. The culture broth comprises the sialic acid which is to be purified as well as biomass (e.g. biological cells and cell debris), medium components, salts and contaminants like other acids and coloured compounds. The purity of the sialic acid to be purified within the culture broth can be <80%. The biological cells contained in the culture broth are biological cells which produce the desired sialic acid (e.g. Neu5Ac) intracellularly and secrete the produced sialic acid into the liquid culture medium. The biological cells can comprise or consist of genetically modified biological cells, for example genetically modified *E. coli* cells. The genetic modification can comprise or consist of a modification to produce a single (desired) sialic acid (e.g. Neu5Ac), especially during the growth phase of said biological cells.

The term "biomass" as used herein refers to the entirety of biological cells present in the fermentation broth at the end of the fermentation step. The biomass includes the cells of the microorganism that produced the desired sialic acid (e.g. Neu5Ac), descendent cells of the microorganism that may have lost their ability to produce the desired sialic acid (e.g. Neu5Ac) during the fermentation step as well as any other cells that are unintentionally present in the fermentation broth at the end of the fermentation step. Hence, essentially all biological cells that are present in the fermentation broth at the end of the fermentation step are separated from the fermentation broth such that the clarified fermentation broth, i.e. the process stream, is substantially free of cells.

The term "process stream" refers to any solution comprising the specific sialic acid which is to be purified.

The term "flowthrough" refers to a solution comprising the sialic acid to be purified which has just passed an ion exchanger material (i.e. a cationic and/or anionic exchanger material), i.e. is a mobile phase comprising sialic acid after a solid phase ion exchanger material has been contacted. In other words, the sialic acid present in the flowthrough has not adsorbed, or has not been absorbed, by the stationary phase.

According to this invention, the difference between a weak cationic ion exchanger material and a strong cationic ion exchanger material is that the chemical groups suitable for ion exchange of the former have a pKa of at least 1 (e.g. pKa from 2 to 5, like that of a carboxylate group) whereas the latter have a pKa of smaller than 1 (e.g. pKa from −4 to 0, like that of a sulfonic acid group).

Production of the Clarified Solution

The biomass can be removed from the fermentation broth by centrifugation and/or filtration.

In suitable centrifugation methods for removing the biomass from the culture broth, the biomass is obtained as a pellet and the supernatant as clarified process stream which is subjected to further treatments. In suitable filtration methods for removing the biomass from the culture broth, the filtrate becomes the clarified process stream. The preferred filtration method for removing biomass is microfiltration and/or ultrafiltration. In ultrafiltration, even smaller particles than with microfiltration can be removed. Optionally, ultrafiltration is cross-flow ultrafiltration.

Microfiltration is a physical separation process wherein a particle-containing fluid is passed through a medium, said medium comprising either a porous substance containing torturous channels to retain particles (depth filtration) and/or a membrane with a specific pore size allowing the passage of particles/molecules that are smaller than said pore size (membrane filtration or dead-end filtration). The term "microfiltration" as used herein refers to a physical separation process wherein biological cells (and cell debris) are removed from the fermentation broth leaving a (clarified) process stream.

Ultrafiltration is a form of membrane filtration that is not fundamentally different from dead-end microfiltration. In ultrafiltration, forces generated by pressure and concentration gradients lead to the removal of particles and large soluble molecules by passing the liquid containing such particles and large soluble molecules through a semipermeable membrane causing the particles and large soluble molecules to be retained in the so-called retentate, while water and low molecular weight solutes such as the sialic acid to be purified pass through the membrane into the permeate (filtrate). Membranes for ultrafiltration are defined by their molecular weight cut-off (MWCO) which describes the maximum molecular weight of a soluble molecule that can pass through the membrane in to the permeate. Any particles, as well as molecules larger than the MWCO, are unable to pass through the membrane are remain in the retentate. Ultrafiltration may be applied in cross-flow mode, where the flow of the liquid is parallel to the membrane surface, or in dead-end mode where the flow of the liquid is perpendicular to the membrane surface.

Non-limiting examples and suitable filters for microfiltration and/or ultrafiltration for removing the biomass from the fermentation broth include SPIRA-CEL® DS MP005 4333, which is a module comprising a polyethersulfone membrane which is spirally wound to provide a compact design and better performance and has a nominal pore size of 0.05 μm for ultrafiltration applications. Suitable membranes for removing the biomass by microfiltration may have a pore size of at least 0.2 μm. Alternatively, the removal of biomass could be done by microfiltration with membranes having a MWCO between 100 and 1000 KDa, preferably between 150 kDa and 500 kDa, to remove the biomass and additional cell debris like bigger proteins. For example FS10-FC FUS1582 (Microdyn-Nadir GmbH, Wiesbaden, DE), a hollow fiber ultrafiltration module using a polyethersulfone membrane (5 m$^2$) with a MWCO of 150,000 Dalton (150 kDa) can be used as alternative.

In an additional and/or alternative embodiment, smaller particles and large soluble molecules are removed from the clarified process stream by a cross-flow ultrafiltration. Here, the clarified process stream can be subjected to an ultrafiltration step using a filter having a MWCO of 10 kDa, for example Spira-Cel DSUP010 (Microdyn-Nadir GmbH, Wiesbaden, DE), a spiral wounded ultrafiltration module using a polyethersulfone membrane (5.7 m2) with a MWCO of 10,000 Dalton (10 kDa).

In summary, the following possibilities for the removal of the biomass from the fermentation broth can be employed in the present invention:

1) Harvest by centrifugation. Insoluble parts are removed from the culture broth in one step. Advantage: Fast removal of insoluble parts;
2) Harvest by microfiltration. Insoluble parts and large molecules above a certain size are removed from the culture broth in one step. Spiral wound membranes or a hollow fiber cross-flow filter can be used in microfiltration. Microfiltration membranes can be used which have a molecular weight cut-off in the range of 500 kDa, more preferably in the range of 150 KDa. Advantage: Fast removal of insoluble parts and large molecules above a certain size;
3) Harvest by ultrafiltration. Insoluble parts, large molecules and small molecules above a certain size are removed from the culture broth in one step. Spiral wound membranes or a hollow fiber cross-flow filter can be used in ultrafiltration. Ultrafiltration membranes can be used which have a molecular weight cut-off in the range of 1.00 kDa, more preferably in the range of KDa. Advantage: Fast removal of insoluble parts, large molecules and small above a certain size;
4) Harvest by centrifugation combined with microfiltration: Insoluble parts and large molecules above a certain size are removed from the culture broth in two steps. Spiral wound membranes or a hollow fiber cross-flow filter can be used in microfiltration. Microfiltration membranes can be used which have a molecular weight cut-off in the range of 500 kDa, more preferably in the range of 150 KDa. Advantage: Fast removal of insoluble parts and large molecules above a certain size without clogging of membranes or filters used in microfiltration;
5) Harvest by centrifugation combined with ultrafiltration: Insoluble parts, large molecules and small molecules above a certain size are removed from the culture broth in two steps. Spiral wound membranes or a hollow fiber cross-flow filter can be used in ultrafiltration. Ultrafiltration membranes can be used which have a molecular weight cut-off in the range of 1.00 kDa, more preferably in the range of 1.0 KDa. Advantage: Fast removal of insoluble parts, large molecules and small molecules above a certain size without clogging of membranes or filters used in ultrafiltration;
6) Harvest by microfiltration combined with ultrafiltration step: Insoluble parts, large molecules and small molecules above a certain size are removed from the culture broth in two steps. Spiral wound membranes or a hollow fiber cross-flow filter can be used in microfiltration and/or ultrafiltration. Microfiltration membranes can be used which have a molecular weight cut-off in the range of 500 kDa, more preferably in the range of 150 KDa. Ultrafiltration membranes can be used which have a molecular weight cut-off in the range of 1.00 kDa, more preferably in the range of 1.0 KDa. Advantage: Fastest removal of insoluble parts, large molecules and small molecules above a certain size with reduced risk of clogging of membranes or filters used in ultrafiltration.

The clarified process stream comprising the sialic acid usually may contain a substantial amount of undesired impurities including (but not limited to) monovalent ions, divalent ions, amino acids, polypeptides, proteins, organic acids, nucleic acids, monosaccharides and/or oligosaccharides.

Steps that are Preferably Absent in the Inventive Process

The inventive process can be characterized in that the process does not comprise a chromatographic separation. The advantage is that the process can be run faster and less expensive because the time and expense for preparing an elution solution and using it to elute the sialic acid from a solid phase is dispensed with.

Furthermore, the inventive process can be characterized in that it does not comprise a use of ethanol and/or ethyl acetate, optionally does not comprise the use of an organic solvent. The advantage is that it can be ensured that the final product, the final sialic acid or composition comprising sialic acid, is free of ethanol and/or ethyl acetate, optionally free of any organic solvent. In addition, the process becomes less expensive and safer for workers.

Moreover, the inventive process can be characterized in that it does not comprise a step of eluting the sialic acid from a stationary phase with a solution comprising an organic solvent. The advantage is that it is possible to keep the purified sialic acid free of any organic solvent. In addition, the process becomes less expensive and safer for workers.

Besides, the inventive process can be characterized in that it does not comprise a use of a heavy metal. The advantage is that it can be ensured that the purified sialic acid is free of heavy metals.

Additionally, the inventive process can be characterized in that it does not comprise a step of heating the fermentation broth, the clarified solution and/or purified solution to a temperature of more than 45° C. The advantage is that compared to prior art processes which employ such a heat treatment step, energy for heating the respective solutions is saved which makes the process more economical and more ecological.

Cationic Ion Exchanger Treatment

Among other impurities, cations can be removed from the clarified process stream by the cationic ion exchanger treatment step of the inventive process, i.e. by applying at least one cation-exchange treatment to the clarified process stream. Specifically, the cations are exchanged to other cations which are bound to the material of the cationic ion exchanger (stationary phase) before the clarified process stream is applied to the cationic ion exchanger treatment step. Importantly, it has been found that the cationic ion exchanger treatment removes ammonia and a part of contaminating proteins from the clarified process stream.

In the cationic ion exchanger treatment step, the positively charged materials can be removed from the cell free culture broth as they bind to the resin. The aqueous solution of the sialic acid is contacted in any suitable manner which allows the positively charged materials to be adsorbed onto the cation exchange material whereas the sialic acid passes through. The resulting liquid, after contacting with the cation exchange resin, contains water, defined cations (those that were immobilized on the cationic ion exchanger material before this step), anions, colouring substances and the desired sialic acid.

The cationic exchanger treatment can be performed with a weak cationic ion exchanger material or with a strong cationic ion exchanger material, preferably it is performed with a strong cationic ion exchanger material.

In the cationic ion exchanger treatment of the inventive process, a strong cationic ion exchanger can be used. Suitable cation-exchange resins for removing positively charged compounds are strongly acidic cation-exchange resins such as resins that comprise a carboxylate group (weak cation exchanger) or sulfonic acid group (strong cation exchanger) attached to a solid backbone (e.g. a polystyrene backbone). Suitable resins include (but are not limited to) Lewatit® S2568(W) (Lanxess A G, Cologne, D E), Dowex® 50WX2 (Merck KGaA, Darmstadt, DE); Amberlite® IR-116 (Japan Organo Co., Ltd.) and Diaion™ SK-102 (Mitsubishi Chemical Industries, Ltd).

The cationic ion exchanger treatment step can be the first step after removal of biomass from the culture medium, i.e. the first step the clarified culture medium is subjected to.

Unspecific cations are preferably replaced by the specific cation $H^+$ or $Na^+$. If the unspecific cations are replaced by $H^+$, the pH of the flowthrough is preferably adjusted to a pH of 6 to 8 before performing a further treatment step (e.g. the anionic ion exchanger treatment), most preferably by addition of NaOH to the flowthrough.

In a preferred embodiment, the cationic ion exchanger material is present in the W form, i.e. the ion exchanging ligand of the cationic ion exchanger material is protonated, before the clarified process stream is applied to the cationic ion exchanger. This effectuates that during cation exchange, cations within the clarified process stream are replaced by $H^+$. Therefore, the pH of the solution after said step (flowthrough) is more acidic than the pH of the solution before said step. Preferably, prior to subsequent purification steps, the pH of the flow-through is elevated to a neutral or almost neutral pH value (e.g. ≥pH 6.5 and ≤pH 7.5). The elevation of the pH can be achieved by adding NaOH to the process stream. By this measure, the sialic acid in the protonated form ($H^+$ form) is converted to a sialic acid salt. In the case of the addition of NaOH, the sodium salt form (Nat form) of sialic acid is obtained.

The cation ion exchanger could be used with any alkali metal ($Li^+$, $Na^+$, $K^+$), alkaline earth metal (such as $Ca^{2+}$, $Mg^{2+}$), ammonium ion or carbonate ion as counter ion. Preferably, sodium ($Na^+$) is the counter ion of the cation ion exchanger. More preferably, hydrogen ($H^+$) is the counter ion. The advantage of hydrogen as counter ion is that upon contacting the cationic ion exchanger material, the protonated form of sialic acid is generated and is found in the flow-through, i.e. in the solution that has passed the cationic ion exchanger material. Subsequently, the protonated form of sialic acid can be neutralized by addition of a base (e.g. NaOH) to the product stream which converts the sialic acid into its salt form (e.g. sodium form). Having the sodium form of sialic acid is beneficial because sodium ions are relatively small cations and can be more easily removed by nanofiltration and/or electrodialysis than larger cations.

Preferably, the cationic exchanger treatment step is carried out before the anionic exchanger treatment step. The advantage of this sequence is that the process stream which has passed the anionic ion exchanger material and comprises the desired sialic acid has a low salt concentration because sialic acid does not bind to the cationic ion exchanger material (i.e. is in the flow-though). Said flow-through can then be applied to an anionic ion exchanger treatment without the necessity of a desalting step. However, in principle, the cationic ion exchanger treatment can also be carried out after the anionic ion exchanger treatment step.

The particle size of the cationic exchanger resin is preferably in the range between 0.1 and 1 mm. This particle size range allows an efficient flow of the used cell free culture broth while the charged materials are still effectively removed by the cation exchange resin. To ensure that an efficient exchange of ions can take place, the flow rate should be preferably between >0.5 and <2.5 fold of the bed volume, more preferably between >1.0 and <2.0 fold of the bed volume. The ion exchange treatment can be carried out in a conventional manner, e.g. batch-wise or continuously, preferably continuously.

The conditions under which the sialic acid passes the cationic exchanger material can be established by adjusting the pH and/or salt concentration of the clarified solution, preferably by adjusting the pH of the clarified solution to a pH in the range of 6 to 8 and/or, if needed, adjusting the salt concentration.

After the cationic ion exchanger treatment and the anionic ion exchanger treatment, the purified solution can comprise the sialic acid, colour-giving substances and salt, wherein the salt is preferably NaCl. According to a preferred embodiment of the invention, in the anionic ion exchanger treatment, an anionic exchanger material in the chloride form is used.

According to a further preferred embodiment of the invention, in the cationic ion exchanger treatment, a cationic ion exchanger material in the hydrogen form is used. It was discovered that using a cation exchanger in hydrogen form ($H^+$ counter ion) is beneficial because a much better binding of salts and contaminating proteins is obtained compared to the cation exchanger material in any other form (counter ion$\neq H^+$). The use of hydrogen form provokes that the flowthrough has a more acidic pH than the solution which was applied to the cationic ion exchanger treatment. However, said pH can easily be raised by the addition of a base, preferably NaOH, to a neutral pH, preferably a pH in the range of 6 to 8. A neutralisation with NaOH is beneficial because the introduced sodium ions are relatively small and can be easily removed by nanofiltration and/or electrodialysis.

The particle size of the cationic exchanger resin should be selected to allow an efficient flow of the used cell free culture broth, while the charged materials are still effectively removed by the cation ion exchange resin. To ensure that an efficient exchange of ions can take place, the flow rate should be preferably between >0.2 and <2.0 fold of the bed volume, more preferably between >0.5 and <1.5 fold of the bed volume. The ion exchange treatment can be carried out in a conventional manner, e.g. batch-wise or continuously, preferably continuously.

The clarified solution can be subjected firstly to the cationic ion exchanger treatment and subsequently to the anionic ion exchanger treatment. This process sequence has the advantage that the cationic ion exchanger material can be in the W form to obtain strong binding of contaminating proteins and after neutralisation with a base (e.g. NaOH), the anionic ion exchanger material can be run with a solution comprising a defined salt form of sialic acid (e.g. the $Na^+$ form of sialic acid).

Anionic Ion Exchanger Treatment

Preferably, the anionic exchanger treatment step is carried out after the cationic exchanger treatment step. However, in principle, it can also be carried out before the cationic exchanger treatment step, i.e. after the process stream was treated with the cationic ion exchanger.

The anionic exchanger step is performed to remove unspecific anions and replace them by specific anions, preferably by the specific anion $Cl^-$ or $OH^-$. If the unspecific anions are replaced by $Cl^-$, the pH of the flowthrough is preferably adjusted to a pH of 6 to 8 before performing a further treatment step (e.g. removing salts from the purified solution by electrodialysis), most preferably by addition of NaOH to the flowthrough.

Anions can be removed from the clarified process stream by an anionic ion exchanger treatment step of the inventive process, i.e. by applying at least one anion ion exchanger treatment to the clarified process stream. The anionic ion exchanger treatment step can be the first step after removal of biomass from the culture medium, i.e. the first step the clarified culture medium is subjected to. Preferably, the anionic ion exchanger treatment is performed in a step after a cationic ion exchanger treatment step.

The negatively charged materials can be removed from the process stream as they bind to the anionic ion exchanger resin. The aqueous solution comprising the desired sialic acid is contacted in any suitable manner which allows the negatively charged materials to be adsorbed onto the anionic exchange material, whereas the sialic acid passes through. The resulting liquid, after contacting with the anionic exchange resin, contains water, defined cations, defined anions, colouring substances and the desired sialic acid. The conditions of the anionic ion exchanger step are such that the sialic acid does not bind to the anion exchanger material, i.e. is present in the flowthrough after having contacted the material.

At the beginning of the anionic ion exchanger treatment, the pH of the product stream is preferably adjusted to pH 6 to 8 (most preferably pH 7). The flowthrough (product stream having passed the anionic ion exchanger material) can have a lower pH, e.g. a pH in the range of 4.5 and 6. At this pH, the sialic acid is present as the sodium form. The pH of the flowthrough can be elevated by adding a base, e.g. NaOH.

During anionic exchange, anions within the clarified process stream can be replaced by $Cl^-$. Therefore, the pH of the process stream becomes slightly more acidic. Preferably, the pH is increased prior to subsequent purification steps, preferably to achieve a neutral or almost neutral pH value (i.e. pH 6.5 and ≤pH 7.5) of the process stream. More preferably, the increase in pH of the process stream is achieved by adding NaOH to the process stream.

The anionic exchanger can be a weak anionic ion exchanger or a strong anionic ion exchanger, preferably a strong anionic ion exchanger.

Suitable strongly basic anion exchange resins are resins that comprise a trimethyl ammonium group or a hydroxyethyl group attached to a solid backbone (e.g. a polystyrene backbone). Suitable resins include (but not limited to) Lewatit® 56368 A, Lewatit® 54268, Lewatit® 55528, Lewatit® 56368A (Lanxess A G, Cologne, D E), Dowex® AG 1×2 (Mesh 200-400), Dowex 1×8 (Mesh 100-200), Purolite® Chromalite CGA100×4 (Purolite GmbH, Ratingen, D E), Amberlite® FPA51 (Dow Chemicals, MI, USA). Preferably, the anion exchange resin is present in chloride form. Suitable weak anion exchange resins are resins that comprise an amino group attached to a solid backbone (e.g. a polystyrene backbone).

The anionic ion exchanger could be used with any base as counter ion, e.g. $HCO_3^-$, $I^-$, $Br^-$, $NO_3^-$. Preferably, the counter ion is hydroxide ($OH^-$). More preferably, the counter ion is chloride ($Cl^-$). The advantage of using chloride as counter ion is that the $Cl^-$ anion is smaller than many other anions that are originally present in the fermentation broth. This effectuates that the chloride anion can be more easily removed from the process stream by electrodialysis. The advantage of using the $OH^-$ anion as counter ion is that when the pH is neutralized with HCl in a step after the anionic ion exchanger treatment, the small anion chloride which can be more easily removed than other anions is introduced into the process stream.

The particle size of the anionic exchanger resin is preferably between 0.1 and 1 mm to allow an efficient flow of the used process stream, while the charged materials are still effectively removed by the anionic exchange resin. To ensure that an efficient exchange of ions can take place, the flow rate should be preferably between >0.5 and <2.5 fold of the bed volume, more preferably between >1.0 and <2.0 fold of the bed volume. The ion exchange treatment can be carried out in a conventional manner, e.g. batch-wise or continuously, preferably continuously.

The conditions under which the sialic acid passes the anionic exchanger material can be established by adjusting the pH and/or salt concentration of the clarified solution, preferably by adjusting the pH of the clarified solution to a pH in the range of 6 to 8 and/or by adjusting the salt concentration, if needed. For example, it has been observed that if a solution comprising the sialic acid is subjected to the anionic ion exchanger treatment which originates from the flowthrough of a cationic ion exchanger treatment with $H^+$ as counter ion and that has been adjusted to pH 6 to 8 by addition of NaOH, the salt concentration of the flow through is sufficiently high to avoid binding of the sialic acid to the anionic ion exchange resin. However, it has been observed that contaminations (e.g. certain proteins, DNA molecules and coloured substances) still bind to the anionic exchange resin under said conditions.

In a preferred embodiment, the purification process comprises a treatment with a cationic exchanger resin in hydrogen ($H^+$) form and an anionic exchanger resin in chloride ($Cl^-$) form. The cationic exchanger resin is preferably a strong cationic exchanger. The anionic exchanger can be a weak or strong anionic exchanger, preferably it is a strong anionic exchanger. Additionally the anionic exchanger material can also be an absorber material. The treatment with both the cationic ion exchanger resin and the anionic ion exchanger resin allows removal of all unspecific ions from the product stream. The unspecific ions can thus be replaced by specific anions, preferably the sodium cation (e.g. introduced by neutralisation of the product stream with NaOH after a contact with a cationic ion exchanger material with $H^+$ as counter ion) and the chloride anion. The sodium cation and the chloride anion are both relatively small ions and can be removed by electrodialysis in a faster and more economical manner than larger ions.

Concentration of the Purified Solution

In a preferred embodiment, the solution after the ion exchanger treatment (flowthrough) which comprises the desired sialic acid (e.g. N-acetylneuraminic acid) is concentrated, preferably by nanofiltration, reverse osmosis and/or vacuum evaporation (e.g. by using a falling film evaporator, a rotating evaporator or a plate evaporator). Reverse osmosis and/or nanofiltration are the preferred methods (e.g. nanofiltration with a nanofiltration membrane having a size exclusion limit of ≥20 Å). Particularly preferred is nanofiltration. The advantage of nanofiltration over reverse osmosis is that nanofiltration achieves faster concentration and also achieves partly removal of salt ions. The advantage of nanofiltration over vacuum evaporation is that no caramelisation reactions occur with the sialic acid, i.e. no coloured caramel bodies are produced during concentration.

The purified solution is most preferably concentrated by nanofiltration, wherein most preferably a nanofiltration membrane is used which has a molecular weight cut-off in the range of 100 to 200 kDa. The advantage of this molecular weight cut-off is that the sialic acid to be purified is held back whereas salt ions can pass through the membrane, i.e. a desalting is effected beside the concentration.

Prior to the concentration of the solution, the sialic acid in the solution can have a concentration of ≤20% (w/w), ≤10% (w/w) or ≤5% (w/w).

In the process, the clarified solution and/or purified solution can be concentrated up to a concentration of ≥100 g/L, preferably ≥200 g/L, more preferably ≥300 g/L, of the sialic acid.

Furthermore, the clarified solution and/or purified solution can be concentrated by nanofiltration at a temperature of <80° C., preferably <50° C., more preferably 4° C. to 45° C., more preferably 10° C. to 40° C., even more preferably 15 to 30° C., most preferably 15 to 20° C.

Moreover, the clarified solution and/or purified solution can be concentrated by reverse osmosis at a temperature of 20° C. to 50° C., more preferably 30° C. to 45° C., most preferably 35° C. to 45° C.

Besides, the clarified solution and/or purified solution can be concentrated at a pressure between >5 bar and <50 bar, preferably at a pressure between >10 bar and <40 bar, more preferably at a pressure between >15 and <30 bar.

Reverse osmosis is a membrane filtration method which removes particles larger than 0.1 nm from the solution (process stream). Only water will be removed from the process stream whereas all other molecules like ions, sugar etc. will be concentrated inside the retentate. By using reverse osmosis, only a raise in the concentration of the sialic acid can be achieved, but no desalting thereof.

In an additional and/or alternative embodiment, the concentration step comprises at least one of the following parameters, optionally all of the following parameters:
 i) concentration is performed up to a concentration of ≥100 g/L, preferably ≥200 g/L, more preferably ≥300 g/L of the sialic acid;
 ii) concentration is performed at a temperature of <80° C., preferably 50° C., more preferably 4° C. to 45° C.; most preferably 4° C. to 40° C., if concentration is performed by nanofiltration;
 iii) concentration is performed at a temperature of <50° C., preferably 20° C. to 45° C.; most preferably 30° C. to 45° C., more preferably 35° C. to 45° C., if concentration is performed by reverse osmosis and/or vacuum evaporation; and
 iv) concentration is operated at a pressure between >5 bar and <50 bar, preferably at a pressure between >10 bar and <40 bar, more preferably at a pressure between >15 and <30 bar.

In a further preferred embodiment of the invention, the solution comprising the sialic acid is concentrated after the electrodialysis step using vacuum evaporation (e.g. by using a falling film evaporator or a plate evaporator), reverse osmosis or nanofiltration (e.g. nanofiltration with a nanofiltration membrane having a size exclusion limit of ≥20 Å), preferably using nanofiltration or reverse osmosis, more preferably using nanofiltration.

Removal of Salts

The process for purifying the sialic acid comprises a step in which salts are removed from the solution, preferably removed from the clarified solution and/or purified solution. Removal of salts can be achieved by subjecting the solution to be desalted to nanofiltration and/or electrodialysis.

Nanofiltration is a membrane filtration method in which the membrane contains nanometer-sized pores. Nanofiltration membranes have pore sizes ranging from 1 to 10 nanometers. The pore size of nanofiltration membranes is smaller than the pore sizes of microfiltration and even smaller than the pore sizes of ultrafiltration membranes, but actually larger than the pore sizes of membranes used for reverse osmosis. Membranes for use in nanofiltration are predominantly created from thin polymer films. Materials that are commonly used include polyethylene terephthalate or metals such as aluminum. Pore densities may range from 1 to $10^6$ pores per $cm^2$. Nanofiltration is used in the method for the purification of the desired sialic acid to increase the concentration of the sialic acid in a solution, e.g. in the clarified solution and/or purified solution. Additionally, a desalting of the solution (process stream) occurs.

Suitable membranes for nanofiltration include polyamide or polypiperazine, thin-film composite membrane material providing a size exclusion in the range of 150 to 300 Da, for example Dow Filnntec™ NF270 (Dow Chemical Company, USA). Such membranes allow high flux. In particular, nanofiltration membranes with a molecular cut-off between 100 and 300 KDa are benegical for raising the concentration of the desired sialic acid (e.g. Neu5Ac) in the process stream. Membranes having this molecular cut-off prevent passing of the sialic acid through the membrane and have the advantage that they also effectuate a desalting because they salt (e.g sodium chloride) which is present in the process stream after the treatment with the ion exchanger material(s) passes the membrane and is separated from the sialic acid. Additional examples of suitable membranes for nanofiltration include Trisep 4040-XN45-TSF (Microdyn-Nadir GmbH, Wiesbaden, DE), GE4040F30 and GH4040F50 (GE Water & Process Technologies, Ratingen, DE).

Nanofiltration was found to efficiently remove significant amounts of contaminants (e.g. salt ions) prior to an electrodialysis treatment of the solution containing the sialic acid. Nanofiltration was also found to be efficient for the removal of low-molecular-weight contaminants from the clarified fermentation broth after removal of biomass from the fermentation broth (e.g. by an ultrafiltration step). The removal of low-molecular-weight components is beneficial for concentrating and demineralizing the solution comprising the sialic acid prior to an ion exchange treatment. The use of nanofiltration for raising the concentration of the sialic acid results in lower energy and processing costs and better product quality due to reduced thermal exposure.

Electrodialysis combines dialysis and electrolysis and can be used for the separation and concentration of ions in solutions based on their selective electromigration through a semipermeable membrane. Industrial electrodialysis applications date back to the early 1960 s when this method was used for the demineralization of cheese whey for inclusion in infant formula. Further applications of electrodialysis include the adjustment of the pH of beverages such as wines, grape must, apple juice and orange juice.

The desalination of brackish water for the production of drinking water and the demineralization of milk whey for infant food production are the most widespread applications of electrodialysis today. The basic principle of electrodialysis consists of an electrolytic cell comprising a pair of electrodes submerged into an electrolyte for the conduction of ions, connected to a direct current generator. The electrode connected to the positive pole of the direct current generator is the anode, and the electrode connected to the negative pole is the cathode. The electrolyte solution then supports the current flow, which results from the movement of negative and positive ions towards the anode and cathode, respectively. The membranes used for electrodialysis are essentially sheets of porous ion-exchange resins with negative or positive charge groups, and are therefore described as cationic or anionic membranes, respectively. The ion exchange membranes usually consist of a polystyrene matrix carrying a suitable functional group (such as sulfonic acid for cationic membranes or a quaternary ammonium group for anionic membranes) cross-linked with divinylbenzene.

The electrolyte can be, for example, an aqueous solution comprising sodium chloride, sodium acetate, sodium propionate and/or or sulfamic acid. The electrolyte surrounds the cathode and anode and serves to allow a flow of an electrical current within the cell. The electrodialysis stack is then assembled in such a way that the anionic and cationic membranes are parallel as in a filter press between two electrode blocks, such that the stream undergoing ion depletion is well separated from the stream undergoing ion enrichment (the two solutions are also referred to as the diluate (undergoing ion depletion) and concentrate (undergoing ion enrichment).

The heart of the electrodialysis process is the membrane stack, which consists of several anion-exchange membranes and cation-exchange membranes separated by spacers, installed between two electrodes. By applying a direct electric current, anions and cations will migrate across the membranes towards the electrodes generating a (desalted) diluate stream and a concentrate stream.

The pore size of the ion-exchange membranes for use in electrodialysis is small enough to prevent diffusion of the product from the diluate stream into the concentrate stream, driven by high concentration differences between the two streams. After separation from biomass and/or exchange of cations and/or anions, proteins and in particular recombinant DNA molecules (ranging in size from fragments to entire genomes) must be quantitatively removed from the desired product.

Electrodialyis used to remove the ions from the aqueous solution whereas the sialic acid will remain inside the process stream. An important advantage of electrodialysis is that recombinant DNA molecules can be completely removed from the solution comprising the sialic acid to be purified. Additionally it has been found that the amount of salt in the process stream could be reduced by electrodialysis significantly. In fact, it has been discovered that sodium chloride can be completely removed from the product stream. This has the advantage that a sialic acid can be provided that is devoid of salt like sodium chloride which prevents any negative influence that a presence of salt (e.g. sodium chloride) can have in the final product e.g. infant food.

Electrodialyis can be performed until a stable conductivity ($nnS/cm^2$) between 0.2 and 10.0 $mS/cm^2$, preferably 0.4 and 5.0 $mS/cm^2$, more preferably 0.5 and 1.0 $mS/cm^2$ is reached. Furthermore, electrodialyis can be performed until the amount of salt (g/l) <10.0 g/l, preferably <5.0 g/l, more preferably <1.0 g/l, most preferably <0.5 g/l is reached.

The electrodialysis can be run under neutral conditions or under acidic conditions. The difference between the two variants lies in the form of the sialic acid. At neutral pH, the sialic acid is present as sodium salt. In this case, the pH value must be controlled during electrodialysis. At acidic pH, the sialic acid is present as a free form (hydrogen form). The advantage of using electrodialysis under under acidic conditions is that of the sodium form of the sialic acid is subjected to said electrodialysis, the free form (hydrogen form) of the sialic acid is present after the electrodialysis. In short, the electrodialysis under acidic conditions not only effectuate a removal of contaminating salt from the sialic acid salt (e.g. sodium salt of sialic acid), but also converts the sialic acid salt into the free form (hydrogen form) of the sialic acid.

By applying neutral condition during electrodialysis, the sodium form of the sialic acid to be purified appears uncharged (interaction of the negatively charged carboxyl group of the sialic acid with the positively charged sodium ion). Before starting the electrodialysis, the pH of the process stream can be adjusted with an acid, preferably with hydrochloric acid (HCl), or a base, preferably sodium hydroxide (NaOH), until a pH of 5.0 to 9.0, preferably 6.0 to 8.0, more preferably 6.5 to 7.5 is reached.

By applying an acidic condition during electrodialysis, the protonated form of the sialic acid appears uncharged (interaction of the negatively charged carboxyl group of the sialic acid with the positively charged proton). Before starting the electrodialysis, the process stream is acidified with an acid, preferably hydrochloric acid (HCl), until a pH of 1.0 to 3.0, preferably 1.5 to 2.5, more preferably 1.8 to 2.2 is reached. Electrodialyis is preferably performed until a stable conductivity ($nnS/cm^2$) and pH is reached.

Electrodialysis can be performed until a stable conductivity ($nnS/cm^2$) between 1.0 and 10.0 $mS/cm^2$, preferably 1.5 and 10.0 $mS/cm^2$, more preferably 2.0 and 8.0 $mS/cm^2$, is reached. During electrodialysis, the pH must be controlled and adjusted with a base, preferably with sodium hydroxide. Under said neutral conditions, electrodialysis can be performed using bipolar membranes. In this case, the sialic acid can be concentrated in a separate electrodialysis concentrate circuit. Thus, the sialic acid can be enriched during electrodialysis.

In the process, after removing salts from the purified solution,
i) the amount of salt in the purified solution can be <10% (w/w), preferably <5% (w/w), more preferably <1% (w/w); and/or
ii) the conductivity can be between 0.2 and 10.0 $mS/cm^2$, preferably between 0.4 and 5.0 $mS/cm^2$, more preferably between 0.5 and 1.0 $mS/cm^2$.

Discolouring of the Clarified and/or Purified Solution

The clarified solution and/or purified solution can be subjected to a step of discolouring, preferably by a treatment with activated charcoal and/or a treatment with a cationic ion exchanger and an anionic ion exchanger which are coupled in series.

The discolouring step can be performed
i) before or after a step of diafiltration and/or concentration of the clarified solution; and/or
ii) before or after a step of electrodialysis and/or diafiltration of the clarified solution.

Optionally, said step is performed after a nanofiltration step and/or before the electrodialysis step.

The advantage of removing colour-giving substances by a treatment with activated charcoal compared to a treatment with a cationic ion exchanger and an anionic ion exchanger (which are coupled in series) is that both electrically charged and electrically uncharged (neutral) colour-giving substances can be removed and electrically uncharged (neutral) oligosaccharides can be removed.

Activated carbon, also called activated charcoal, is a form of carbon that has been processed to have small, low-volume pores that increase the surface area available for adsorption. Typically, just one gram of activated carbon has a surface area greater than 3000 $m^2$ as determined by gas adsorption, due to its high degree of micro porosity.

A carbohydrate substance like a monosaccharide or oligosaccharide tends to be bound to the surface of charcoal particles from an aqueous solution. Interaction of oligosaccharides with activated charcoal is much stronger than interaction of monosaccharides. This behaviour is caused by their structure and effectuates that a sialic acid (e.g. Neu5Ac) is bound weaker, i.e. to a smaller amount, to the activated charcoal than a contaminating oligosaccharide. Besides oligosaccharides, coloured materials are adsorbed to the activated charcoal. Other water soluble materials like salts are bound in a weaker manner and elute from the activated charcoal with the desired sialic acid by washing the charcoal with water (after incubation). After the elution with water, the adsorbed oligosaccharides and coloured substances still remain bound to the activated charcoal. Therefore, removal of contaminating oligosaccharides and coloured contaminants is possible by the treatment step with activated charcoal. In summary, the activated charcoal step removes colorants, other impurities and reduces the amount of water soluble contaminants, such as salt.

Suitable activated charcoals for removing colour giving compounds, oligosaccharide or contaminates are (but not limited to) granulated activated charcoals like Norit GAC830EN (Carbot Cooperation) and Epibon Y 12×40 spezial (Donaucarbon) or powdered activated charcoal like Norit DX1, Norit SA2 (Carbot Cooperation) and Carbopal MB 4 (Donaucarbon).

The removal of colour-giving substances by a treatment with a cationic ion exchanger and an anionic ion exchanger (which are coupled in series) has the advantage compared to a treatment with activated charcoal that not only colour-giving substances can be removed from the solution, but unspecific salt ions in the solution can be exchanged to specific salt ions like e.g. Nat and Cl$^-$. The advantage of said ion exchange is that the desalting process can become more efficient ($Na^+$ and $Cl^-$ are small ions compared to other possible ions and thus may be removed more easily by a desalting treatment step). A further advantage is that a negative influence of certain unspecific salts on crystallisation of the sialic acid can be avoided.

The ion exchanger treatment is performed such that the charged materials and the colour-giving substances are adsorbed onto the respective ionic exchange material whereas the sialic acid passes the respective ionic exchange material, i.e. is located in the flowthrough. The resulting liquid (flowthrough) contains water, a small amount of defined ions, a reduced amount of colour-giving substances and the sialic acid.

The cationic exchanger can be a weak cationic ion exchanger or a strong cationic ion exchanger, preferably it is a strong cationic ion exchanger.

Suitable cation-exchange resins are strongly acidic cation-exchange resins such as (but not limited to) Lewatit® S2568(W) (Lanxess A G, Cologne, D E), Dowex® 50WX2 (Merck KGaA, Darmstadt, D E); Amberlite® IR-116 (Japan Organo Co., Ltd.) and Diaion™ SK-102 (Mitsubishi Chemical Industries, Ltd).

The cationic ion exchanger could be used with any alkali metal ($Li^+$, $Na^+$, $K^+$), alkaline earth metal (such as $Ca^{2+}$, $Mg^{2+}$), ammonium ion or carbonate ion as counter ion. Preferably, the sodium ion ($Na^+$) is the counter ion.

The anionic exchanger can be a weak anion exchanger or a strong anionic exchanger, preferably it is a strong anionic ion exchanger.

Suitable anion exchange resins are strongly basic (type I) anion exchange resins such as (but not limited to) Lewatit® 56368 A, Lewatit® 54268, Lewatit® S5528, Lewatit® 56368A (Lanxess A G, Cologne, D E), Dowex® A G 1×2 (Mesh 200-400), Dowex® 1×8 (Mesh 100-200), Purolite®

Chromalite CGA100×4 (Purolite GmbH, Ratingen, D E), Amberlite® FPA51 (Dow Chemicals, MI, USA). Preferably, the anion exchange resin is present in chloride form.

The anionic ion exchanger could be used with any base as counter ion, e.g. $HCO^-_3$, $I^-$, $Br^-$, $NO^-_3$. Preferably, hydroxide ($OH^-$) is used as counter ion. More preferably, chloride ($Cl^-$) is used as counter ion.

Within the coupled series of the cationic ion exchanger and the anionic ion exchanger, the anionic ion exchanger can be located upstream or downstream of the cationic ion exchanger. Preferably, the anionic ion exchanger is located downstream of the cationic ion exchanger in the coupled series. Thus, a solution passing the series firstly passes the cationic ion exchanger and then passes the anionic ion exchanger.

The pH of the process stream having passed the cationic ion exchanger and/or anionic ion exchanger (i.e. the respective flowthrough) is preferably >2.0 and <10.0, more preferably >3.0 and 9.0, most preferably >4.0 and <8.0.

The particle size of the ionic exchanger resin should be selected to allow an efficient flow of the process stream, while the charged materials and the colour-giving substances are still effectively removed by the ion exchange resin. To ensure that an efficient exchange of ions can take place, the flow rate should be preferably between >0.2 and <2.0 fold of the bed volume, more preferably between >0.5 and <1.5 fold of the bed volume and most preferably >0.75 and <1.2 fold of the bed volume. The ion exchange treatment can be carried out in a conventional manner, e.g. batch-wise or continuously, preferably continuously.

Sterile Filtration and/or Removal of Endotoxins

In a preferred embodiment of the invention, the purified solution is sterile filtered and/or subjected to endotoxin removal, preferably by filtration of the purified solution through a 10 kDa filter module. As an example, the purified solution containing the sialic acid is filter-sterilized and/or subjected to an endotoxin removal step by filtration of the purified solution through a 3 kDa filter or through a 6 kDa filter. The removal of endotoxins is necessary if the sialic acid is intended for human consumption.

Conversion of Free Sialic Acid (Hydrogen Form) into its Salt Form

In order to convert the free acid form of the sialic acid or a sodium salt form of the sialic acid to a different salt form, the cationic ion exchanger can be used with any alkali metal ($Li^+$, $Na^+$, $K^+$), alkaline earth metal (such as $Ca^{2+}$, $Mg^{2+}$), ammonium ion or carbonate ion to form the corresponding salts. Sialic acid in the salt form (especially in the sodium form) is significantly more stable than in the free acid form because it has been found that unlike the free acid form, no discoloration reaction in an aqueous medium occurs.

The sialic acid comprised in the clarified solution and/or purified solution is preferably converted into its sodium form, preferably by is treating the purified solution with a strong cationic ion exchanger material in the sodium form. The advantage of the sodium form is that it is a pH-neutral substance, i.e. when dissolved in water, the pH of water remains neutral. On the contrary, when the free form of a sialic acid (hydrogen form) is dissolved in water, the pH of water becomes acidic. It has been observed that under acidic conditions and at a temperature above 10° C., a sialic acid (especially Neu5Ac) is prone to discouloring, i.e. susceptible to forming coloured compounds. Since the sodium form of the sialic acid does not show the pH-decreasing behaviour, the sodium form is more stable against forming coloured compounds.

Conversion of Sodium Form of Sialic Acid into its Free Form (Hydrogen Form)

The sodium salt of the sialic acid can be converted into the free sialic acid (protonated form) by another cationic exchange step. During this step, sodium ions ($Na^+$) associated to the sialic acid or within the clarified process stream are replaced by protons ($H^+$). This exchange effectuates that the pH of the process stream becomes more acidic.

The positively charged sodium ions can be removed from the sialic acid by treating the solution comprising the sodium salt of sialic acid with a cationic ion exchanger in hydrogen ($H^+$) form. The cationic ion exchanger can be a weak cationic ion exchanger or a strong cationic ion exchanger, preferably it is a strong cationic ion exchanger. In this step, the positively charged sodium ions from the sialic acid can be removed from the deprotonated sialic acid molecules and bind to the resin wherein $H^+$ ions are released from the resin and can protonate the deprotonated sialic acid. The aqueous solution of the sialic acid is contacted in any suitable manner which allows the exchange of sodium ions to hydrogen ions and adsoption of the sodium ions onto the cation exchange material, whereas the sialic acid passes through. The resulting liquid, after contacting with the cation exchange resin contains the protonated sialic acid.

Suitable cationic-exchange resins for removing positively charged sodium from the sialic acid solution are strongly acidic cation-exchange resins such as (but not limited to) Lewatit® S2568(W) (Lanxess A G, Cologne, D E), Dowex® 50WX2 (Merck KGaA, Darmstadt, D E); Amberlite® IR-116 (Japan Organo Co., Ltd.) and Diaion™ SK-102 (Mitsubishi Chemical Industries, Ltd).

Instead of converting a salt of the sialic acid to the free acid or to a different salt form by a cationic ion exchanger treatment, an electrodialysis step can be performed instead. Electrodialysis can used to remove the sodium from the process stream under acidic conditions whereas the sialic acid will remain as protonated form inside the process stream.

By applying an acidic condition during electrodialysis, the sialic acid can be protonated such that it appears uncharged (protonation of the carbonyl group). Before starting the electrodialysis, the process stream is acidified with an acid, preferably hydrochloric acid (HCl), until a pH of 1.0 to 3.0, preferably 1.5 to 2.5, more preferably 1.8 to 2.2 is reached. Electrodialyis is preferably performed until a stable conductivity ($mS/cm^2$) and pH is reached.

Providing a Spray-Dried Form of the Sialic Acid

In a preferred embodiment, the purified solution is spray-dried. The purified solution which is subjected to spray-drying preferably comprises the sialic acid in the sodium form.

The purified solution may be spray-dried at a concentration of the sialic acid of 5-35% (w/w), preferably 10-30% (w/w), more preferably 15-25% (w/w). The inlet temperature can be in the range of 110-150° C., preferably 120-140° C., more preferably 125-135° C. The outlet temperature can be in the range of 60-80° C., preferably 65-70° C.

Providing a Crystallized Form of the Sialic Acid

The purified solution can be subjected to crystallisation, preferably by addition of acetic acid to the purified solution. According to this embodiment, sialic acid is provided preferably in the dihydrate crystal form.

In order to follow the embodiment of the invention, a method for crystallizing the sialic acid from aqueous solutions will be described herein. It has been discovered that a sialic acid (like e.g. Neu5Ac) can be selectively crystallized from a biocatalyis approach using enzymes or fermentation (culture) broth as dihydrate form.

In a preferred embodiment, the purified (aqueous) solution of the sialic acid to be used for crystallisation has a carbohydrate content of more than 20% (w/w), preferably more than 30% (w/w), preferably more than 40% (w/w), particularly more than 50% (w/w). Alternatively, the sialic acid concentration in the purified (aqueous) solution to be used for the crystallization is 450-600 g/l, preferably 500-550 g/l.

The above concentration ranges and ratios can be achieved in a conventional manner by concentrating the aqueous process stream from the culture broth, preferably after removing, e.g. cells, colour giving substances, salts and/or charged molecules from the culture broth by using previously described methods.

Concentration of the sialic acid containing solution can be achieved by vacuum evaporation (e.g. by using a rotating evaporator or a plate evaporator) or by nanofiltration. For starting crystallization, seeding crystals are added to said concentrated sialic acid solution at a temperature between 20'C and 50° C., preferably at 25° C.

The solution comprising the sialic acid can have a carbohydrate concentration of >50% (w/w). The crystallization approach can be incubated under vacuum, preferably under at least one of the following conditions:
  i) a pressure of <200 mbar, more preferably at a pressure of <100 mbar, particularly at a pressure of <50 mbar;
  ii) a product temperature between 15° C. to 60° C., preferably between 20° C. to 45° C., more preferably between 25° C. to 40° C., particularly between 30'C and 35° C.; and
  iii) an incubation time until the carbohydrate concentration has reached >60%, preferably <70%, or a viscous crystallization pulp occurs.

An organic solvent, preferably isopropanol, can be added to the crystallisation solution. To enhance the crystallization process, 1 liter of crystallization material is mixed with 0.5 to 3 l, preferably 0.7 to 2.0 l, more preferably 1.0 to 1.5 l, of isopropanol. The resulting crystallization approach, having a starting temperature between 20° C. and 30° C., is cooled down without or with stirring to a temperature between 0 to 15° C., preferably to 2 to 12° C., more preferably to 4 to 8'C. After the preferred temperature has been reached, the crystallization approach is incubated without or with stirring for 2 to 48 h, preferably 6 to 36 h, more preferably 12 to 24 h, at the selected temperature.

The sialic acid crystals can be removed from the liquid phase by filtering with or without vacuum or by centrifugation. To remove the remaining mother liquor, the crystals can be washed with an organic solvent, e.g. ethanol, methanol and/or isopropanol, preferably isopropanol. To remove the remaining mother liquor, 1 kg of crystallized sialic acid (e.g. N-acetylneuraminic acid) is washed with 0.5 to 3 l, preferably 0.7 to 2.0 l, more preferably 1.0 to 1.5 l, isopropanol.

The resulting crystals are dried for 4 to 48 h, preferably 8 to 36 h, more preferably 12 to 24 h, or until no change in weight can be observed. The drying temperature can lie between 10'C and 80'C, preferably between 20'C and 70'C, more preferably between 30'C and 60'C, particularly between 40' and 50'C.

For crystallization of the sialic acid (e.g. Neu5Ac) as dihydrate from an aqueous solution, a second alternative method for crystallizing of the sialic acid from aqueous solutions as dihydrate will be described herein.

To start crystallization, seeding crystals are added to the concentrated sialic acid at a temperature between 20'C and 50° C., preferably at 25'C. The solution of the sialic acid can have a carbohydrate concentration of >50% (w/w). The crystallization approach should be incubated under stirring until crystallization occurs, preferably for 0.5 to 2 hours, more preferably for 1 to 1.5 hours.

An organic solvent, preferably isopropanol, is added to the crystallisation solution. To enhance the crystallization process, 1 liter of crystallization material is mixed with 0.5 to 6.0 l, preferably 1.0 to 4.0 l, more preferably 1.5 to 2.5 l, isopropanol. The resulting crystallization approach, having a starting temperature between 20° C. and 30° C., is cooled down without or with stirring to a temperature between 0 to 15° C., preferably to 2 to 12° C., more preferably to 4 to 8'C. After the preferred temperature has been reached, the crystallization approach is incubated without or with stirring for 2 to 48 h, preferably 6 to 36 h, more preferably 12 to 24 h, at the selected temperature.

The sialic acid crystals can be removed from the liquid phase by filtering with or without vacuum or centrifugation. To remove the remaining mother liquor, the crystals can be washed with an organic solvent e.g. ethanol, methanol and/or Isopropanol, preferably isopropanol. To remove the remaining mother liquor, 1 kg of crystallized sialic acid (N-acetylneuraminic acid) is washed with 0.5 to 3 l, preferably 0.7 to 2.0 l, more preferably 1.0 to 1.5 l, isopropanol.

The resulting crystals are dried for 4 to 48 h, preferably 8 to 36 h, more preferably 12 to 24 h or until no change in weight can be observed. Drying temperature is selected between 10° C. and 80° C., preferably between 20° C. and 70° C., more preferably between 30° C. and 60° C., particularly between 40° and 50° C.

An alternative method for selectively crystallizing of the sialic acid (e.g. Neu5Ac) from aqueous solutions will be described herein. It has been discovered that a sialic acid can be selectively crystallized from a biocatalyis approach using enzymes or fermentation (culture) broth by adding glacial acid.

In a preferred embodiment, the purified (aqueous) solution of the sialic acid to be treated with acetic acid has a carbohydrate content of more than 10% (w/w), preferably more than 20% (w/w), more preferably more than 30% (w/w), particularly around 35 to 40% (w/w). Alternatively, the sialic acid concentration in the purified (aqueous) solution to be treated with acetic acid is 250-350 g/l, preferably 290-330 g/l.

The above concentration ranges and ratios can be achieved in a conventional manner by concentrating the aqueous process stream from the culture broth, preferably after removing, e.g. cells, colour-giving substances, salts and/or charged molecules from the culture broth by using previously described methods.

Concentration of the sialic acid containing solution can be achieved by vacuum evaporation (e.g. by using a rotating evaporator or a plate evaporator) or by nanofiltration.

To the resulting aqueous solution, acetic acid is added at a temperature between 20° C. and 50° C., preferably at 25° C. The acetic acid is added completely at one step or in portions to the aqueous solution over a period of 0.5 to 2 hours, preferably 1 to 1.5 hours. Preferably, the aqueous solution is continuously stirred at the same temperature while the acetic acid is being added while crystallization occurs and preferably also after said point in time.

Preferably, about 5-25 l glacial of acetic acid is used for each kilogram of the sialic acid in aqueous solution. Thus, for an aqueous solution of 250-350 g/l, preferably 290-330 grams/liter, of the sialic acid, the carbohydrate content of which is more than 30% (w/w), at least about 5-25 litres, preferably 7-20 litres, more preferably 10-18 litres, particularly 12-16 litres, of acetic acid are used per kilogram of the sialic acid in the aqueous solution.

The resulting crystallization approach, starting temperature between 20'C and 50° C., is cooled down without or with stirring, to a temperature between 0 to 15° C., preferably to 2 to 12° C., more preferably to 4 to 8° C. After the preferred temperature has been reached, the crystallization approach is incubated without or with stirring for 2 to 48 h, preferably 6 to 36 h, more preferably 12 to 24 h, at the selected temperature.

The sialic acid crystals are removed from the liquid phase by filtering with or without vacuum or centrifugation. To remove the remaining acetic acid, the crystals will be washed with an organic solvent e.g. ethanol, methanol and/or isopropanol, preferably with isopropanol. To remove the remaining acetic acid 1 kg of the crystallized sialic acid is washed with 0.5 to 3 l, preferably 0.7 to 2.0 l, more preferably 1.0 to 1.5 l isopropanol.

The resulting crystals are dried for 4 to 48 h, preferably 8 to 36 h, more preferably 12 to 24 h or until no change in weight can be observed. Drying temperature is selected between 10° C. and 80'C, preferably between 20'C and 70'C, more preferably between 30'C and 60'C, particularly between 40' and 50° C.

Providing a Lyophilized Form of the Sialic Acid

The purified solution comprising the sialic acid can also be lyophilized. In said lyophilisation, the purified solution comprising the sialic acid is frozen and then the pressure is reduced such that the frozen water sublimes directly from the solid phase to the gas phase. This method usually produces a hygroscopic sialic acid powder.

Compositions and Products Provided by the Invention

According to the invention, a composition is provided which comprises
a) at least 98 wt.-% of a sialic acid;
b) at most 1 wt.-% organic solvent; and
c) at most 1 wt.-% salts different to the salt form of the sialic acid.

In a preferred embodiment, the composition comprises
a) 98.50 to 100.00 wt.-% of the sialic acid, preferably 99.00 to 100.00 wt.-% of the sialic acid, more preferably 99.50 to 100.00 wt.-% of the sialic acid, optionally 99.70 to 99.90 wt.-% of the sialic acid; and/or
b) 0.00 to 1.00 wt.-% organic solvent, preferably 0.00 to 0.50 wt.-% organic solvent, more preferably 0.00 to 0.40 wt.-% organic solvent, optionally 0.10 to 0.20 wt.-% organic solvent; and/or
c) 0.00 to 1.00 wt.-% salts different to a salt form of the sialic acid, preferably 0.00 to 0.50 wt.-% salts different to a salt form of the sialic acid, more preferably 0.00 to 0.40 wt.-% salts different to a salt form of the sialic acid, optionally 0.10 to 0.20 wt.-% salts different to a salt form of the sialic acid.

Preferably, the composition comprises (only)
a) 0.00 to 0.50 wt.-% proteins, more preferably 0.00 to 0.40 wt.-% proteins, optionally 0.10 to 0.20 wt.-% proteins; and/or
b) 0.00 to 0.50 wt.-% DNA, more preferably 0.00 to 0.40 wt.-% DNA, optionally 0.10 to 0.20 wt.-% DNA.

The composition can be characterized in that the sialic acid is present in amorphous form or in crystalline form, preferably in granulate form or in crystalline form, more preferably in spray-dried form or in crystalline form. The crystalline form is preferably the dihydrate crystal form.

A food composition, preferably an infant food formula, a toddler food formula or a medical nutrition product, is provided, wherein the food composition comprises a sialic acid and at least one human milk oligosaccharide.

The food composition can comprise at least one sugar selected from the group consisting of 2'-fucosyllactose, 3-fucosyllactose, lacto-N-tetraose, 3'-sialyllactose, 6'-sialyllactose and lacto-N-neotetraose.

The food composition can be
i) a liquid food composition and comprises the sialic acid at a concentration of 1 mg/l to 2 g/l, more preferably at a concentration of 5 mg/l to 1.5 g/l, even more preferably at a concentration of 20 mg/l to 1 g/l, most preferably at a concentration of 50 mg/l to 0.7 g/l; or
ii) a solid food composition and comprises the sialic acid at a concentration of 5 mg/kg to 15 g/kg, more preferably at a concentration of 25 mg/kg to 10 g/kg, even more preferably at a concentration of 100 mg/kg to 10 g/kg, most preferably at a concentration of 375 mg/kg to 5.25 g/kg.

The food composition can comprise
i) at least one neutral human milk oligosaccharide, preferably at least one neutral human milk oligosaccharide selected from the group consisting of 2'-fucosyllactose, 3-fucosyllactose, lacto-N-tetraose and lacto-N-neotetraose, most preferably all of said neutral human milk oligosaccharides; and
ii) at least one acidic human milk oligosaccharide, preferably at least one acidic human milk oligosaccharide selected from the group consisting of 3'-sialyllactose and 6'-sialyllactose, most preferably all of said acidic human milk oligosaccharides; and
iii) L-fucose.

The composition can further comprise at least one substance, optionally all substances, selected from the group consisting of lactose, whey protein, biotin, skimmed milk, vegetable oil, skimmed milk powder, oil of *Mortierella alpine*, fish oil, calcium carbonate, potassium chloride, vitamin C, sodium chloride, vitamin E, iron acetate, zinc sulfate, niacin, calcium-D-panthothenate, copper sulfate, vitamin A, vitamin B1, vitamin B6, magnesium sulphate, potassium iodate, folic acid, vitamin K, sodium selenite and vitamin D.

The food composition can comprise at least one substance selected from the group consisting of a protein source, a vitamin, an oil, a mineral, an enzyme, a further carbohydrate and a probiotic strain.

The composition can be a composition selected from the group consisting of a medical food composition, a dietary supplement, a sachet product, a liquid ready-to-use infant nutrition product, a liquid ready-to-use toddler nutrition product, a granulated product, a spray-dried infant formula product and combinations thereof.

Further provided is a liquid, ready-to-use infant or toddler nutrition product comprising a sialic acid at a concentration of 1 mg/l to 2 g/l, L-fucose and
i) at least one neutral human milk oligosaccharide selected form the group consisting of 2'-fucosyllactose, 3-fucosyllactose, difucosyllactose, lacto-N-tetraose and lacto-N-neotetraose; and/or
ii) at least one acidic human milk oligosaccharide selected from the group consisting of 3'-sialylactose or 6'-sialyllactose.

The invention also provides a spray-dried infant formula product comprising a sialic acid at a concentration of 5 mg/kg to 15 g/kg, L-fucose and
i) at least one neutral human milk oligosaccharides selected form the group consisting of 2'-fucosyllactose, 3-fucosyllactose, difucosyllactose, lacto-N-tetraose and lacto-N-neotetraose; and/or ii) at least one acidic human milk oligosaccharide selected from the group consisting of 3'-sialyllactose and 6'-sialyllactose.

Moreover, a dietary supplement is provided, comprising a sialic acid and at least one neutral HMO selected from the group consisting of 2'-fucosyllactose, 3-fucosyllactose, difucosyllactose, lacto-N-tetraose and lacto-N-neotetraose.

According to the invention, a premix for a food product (e.g. premix for an infant food formula) is provided which comprises a sialic acid (e.g. Neu5Ac) and at least one substance selected from the group consisting of a protein source, a vitamin, an oil, a mineral, an enzyme, a further carbohydrate (e.g. a carbohydrate different to the sialic acid already present in the premix) and a probiotic strain. More preferably, the premix comprises all of said substances.

The protein source can be selected from the group consisting of whey, corn soya blend (CSB), protein hydrolysates and combinations thereof.

The vitamin can be selected from the group consisting of vitamin A, thiamine, riboflavin, vitamin B12, folate and combinations thereof.

The oil can be selected from the group consisting of palm oil, DHA, arachidonis acid and combinations thereof.

The mineral can be selected from the group consisting of potassium chloride, potassium iodate, zinc oxide and combinations thereof.

The enzyme can be selected from the group consisting of amylase, amyloglucosidase and combinations thereof.

The carbohydrate can be selected from the group consisting of a human milk oligosaccharide (HMO), a galactooligosaccharide (GOS), inulin (FOS), L-fucose, a further sialic acid, lactose and combinations thereof.

The probiotic strain can be selected from the group consisting of (encapsulated) *Lactobacillus, Bifidobacterium* strain and combinations thereof.

The premix can be in the form of a spray-dried, granulated or liquid (syrup) product.

According to the invention, a pharmaceutical composition, preferably a pharmaceutical composition for use in preventing or treating at least one of a viral infection, a bacterial infection, a memory loss and dysbiosis, is provided.

The pharmaceutical composition comprises a composition according to the invention and optionally comprising at least one sugar different to a sialic acid and/or at least one probiotic bacterial strain, wherein the at least one sugar is preferably at least one sugar selected from the group consisting of lactose, lactulose, inulin and sucrose.

Release formulations of sialic acid, or a pharmaceutically acceptable salt, solvate, or ester thereof, are known in the prior art and are described e.g. in WO 2012/009474 and WO 2013/109906, the contents of which are hereby incorporated by reference.

Exemplary Food Composition

The inventive process provides the desired sialic acid of sufficient purity to allow its use in food or feed applications, in particular useful for inclusion into infant and toddler nutrition products. The obtained sialic acid, in particular Neu5Ac, can used for the preparation of a infant formula by mixing it with components of an infant base formula. The infant formula can be a powder formula or a ready-to-used liquid infant formula.

The base formula can have at least one, optionally all, of the following components:

Base formula: Components of a representative base formula:

Skimmed milk
Vegetable oils (palm oil, rapeseed oil, sunflower oil)
Skimmed milk powder
Oil of *Mortierella alpine*
Fish oil
Calcium carbonate
Potassium chloride
Vitamin C
Sodium chloride
Vitamin E
Iron acetate
Zinc sulfate
Niacin
Calcium-D-panthothenate
Copper sulfate
Vitamin A
Vitamin B1
Vitamin B6
Magnesium sulfate
Potassium iodate
Folic acid
Vitamin K
Sodium selenite
Vitamin D Use of the Inventive Composition A use of the inventive composition in the manufacture of a food composition and/or pharmaceutical composition is suggested.

With reference to the following figures and examples, the subject according to the invention is intended to be explained in more detail without wishing to restrict said subject to the special embodiments shown here.

FIG. 1 shows an example of an inventive process for purification of the sialic acid N-acetylneuraminic acid. After fermentation, the fermentation broth is clarified by centrifugation and/or filtration. The clarified fermentation broth is subjected to an ionic exchanger treatment. The flow-through of the ionic exchanger treatment is then subjected to diafiltration and/or concentration. After said step, the solution comprising the sialic acid is passed over activated charcoal. Then, the solution comprising the sialic acid is subjected to electrodialysis and/or diafiltration. Subsequently, the solution comprising the sialic acid is subjected to spray-drying or crystallization.

Figure 2:
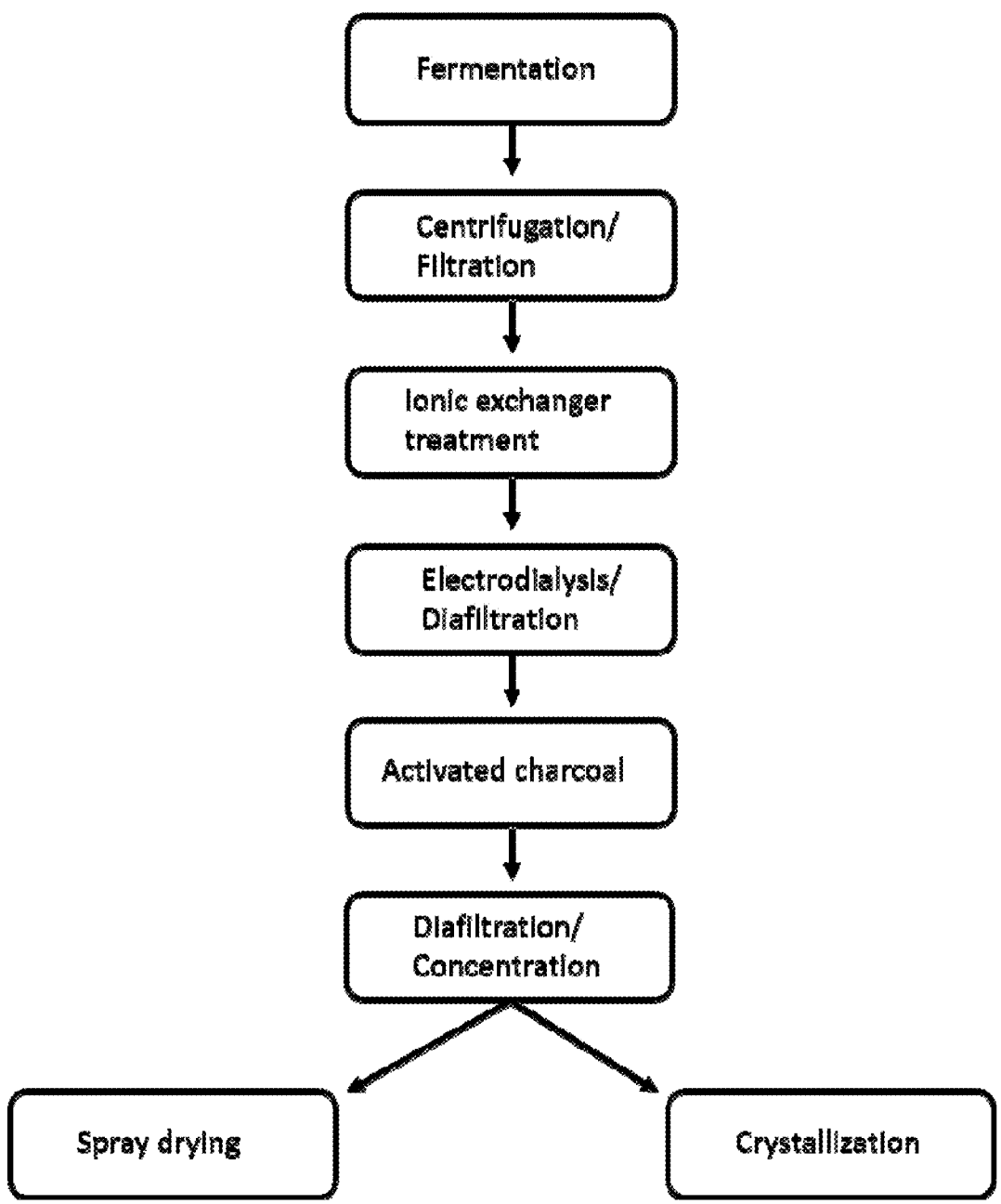

FIG. 2 shows an example of a second inventive process for purification of the sialic acid N-acetylneuraminic acid. After fermentation, the fermentation broth is clarified by centrifugation and/or filtration. The clarified fermentation broth is subjected to an ionic exchanger treatment. The flow-through of the ionic exchanger treatment is then subjected to electrodialysis and/or diafiltration. After said step, the solution comprising the sialic acid is passed over activated charcoal. Then, the solution comprising the sialic acid is subjected to diafiltration and/or concentration. Subsequently, the solution comprising the sialic acid is subjected to spray-drying or crystallization.

Figure 3:
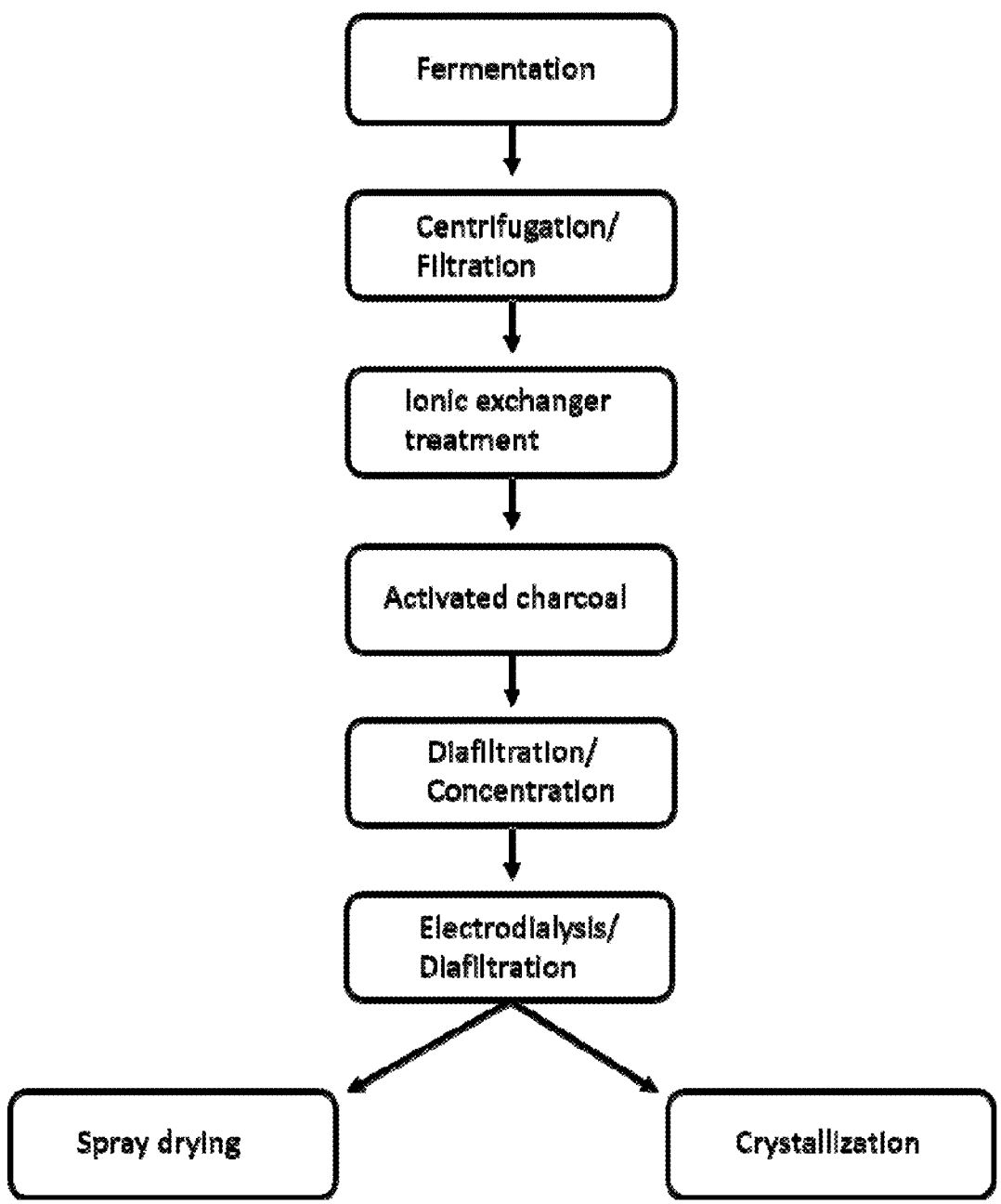

FIG. 3 shows an example of a third inventive process for purification of the sialic acid N-acetylneuraminic acid. After fermentation, the fermentation broth is clarified by centrifugation and/or filtration. The clarified fermentation broth is subjected to an ionic exchanger treatment. The flow-through of the ionic exchanger treatment is then passed over activated charcoal. After said step, the solution comprising the sialic acid is subjected to diafiltration and/or concentration. Then, the solution comprising the sialic acid is subjected to electrodialysis and/or diafiltration. Subsequently, the solution comprising the sialic acid is subjected to spray-drying or crystallization.

Figure 4:
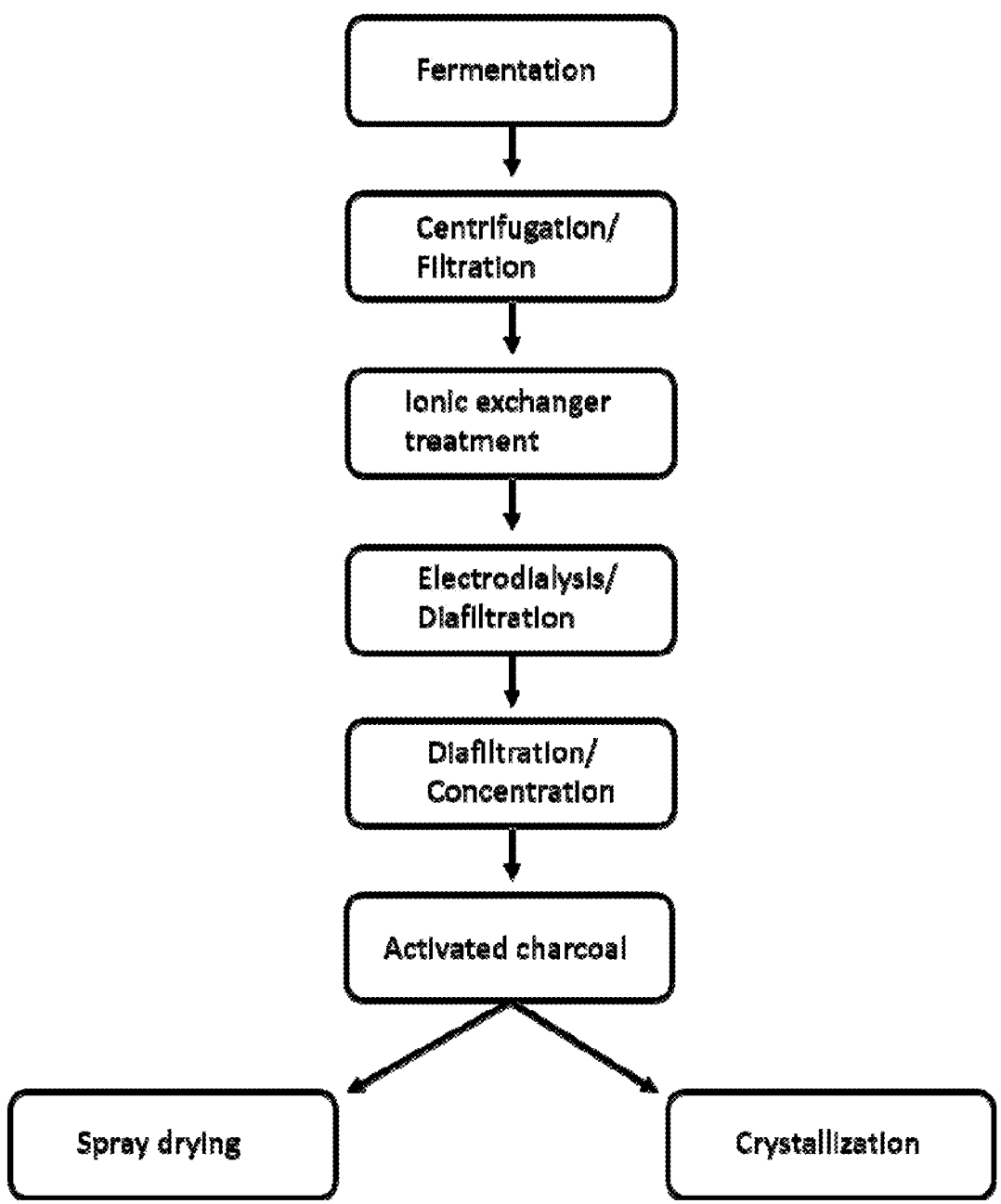

FIG. 4 shows an example of a fourth inventive process for purification of the sialic acid N-acetylneuraminic acid. After fermentation, the fermentation broth is clarified by centrifugation and/or filtration. The clarified fermentation broth is subjected to an ionic exchanger treatment. The flow-through of the ionic exchanger treatment is then subjected to electrodialysis and/or diafiltration. After said step, the solution comprising the sialic acid is subjected to diafiltration and/or concentration. Then, the solution comprising the sialic acid is passed over activated charcoal. Subsequently, the solution comprising the sialic acid is subjected to spray-drying or crystallization.

Figure 5:
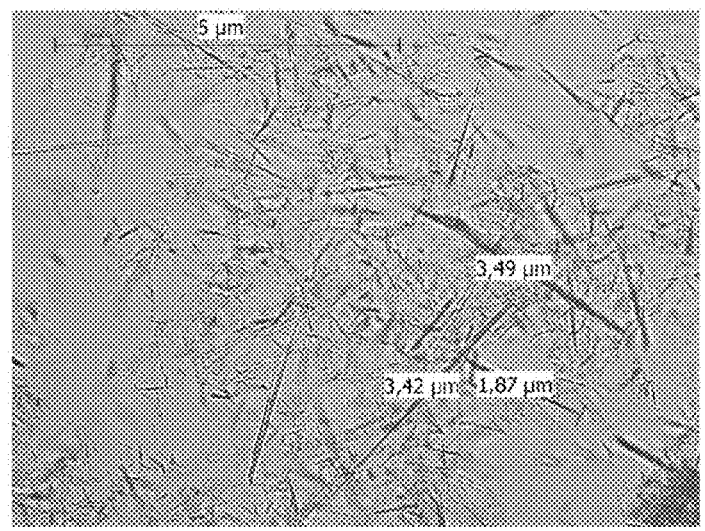
Figure 5:
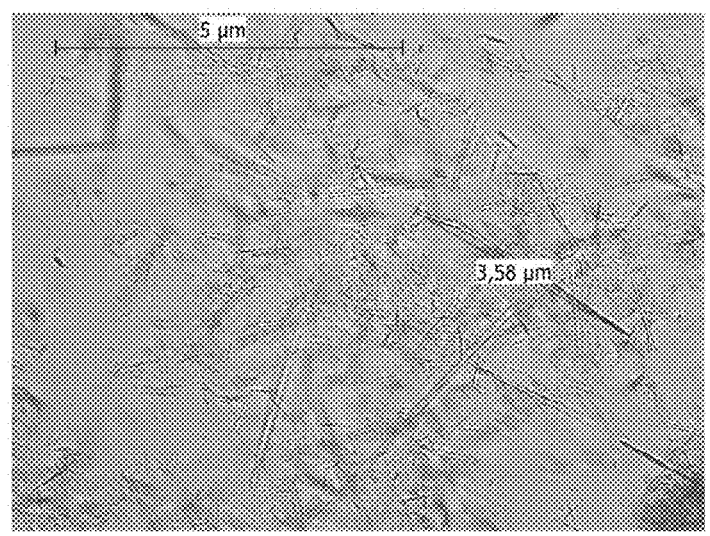

FIG. 5 shows a microscopic picture of crystals of N-acetylneuraminic acid. It can be seen that N-acetylneuraminic acid forms small needles with a length of 2 to 8 μm.

Figure 6:
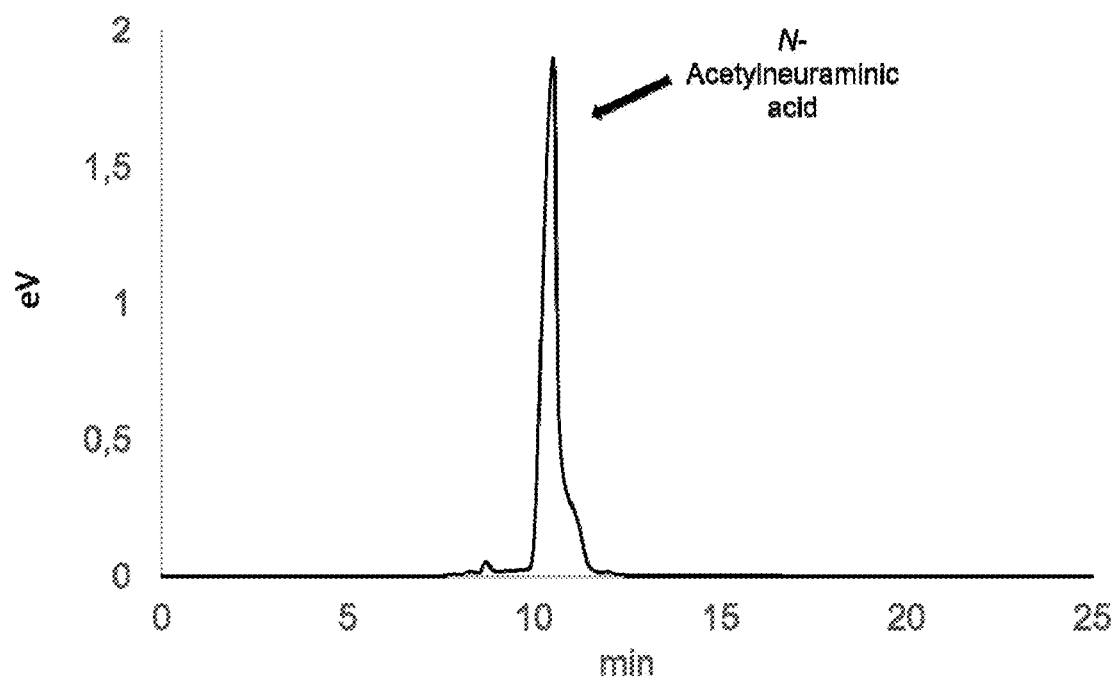

FIG. 6 shows an HPLC diagram which was recorded for N-acetylneuraminic acid that has been crystallized as dihydrate. The purity of the crystallized N-acetylneuraminic acid is detected as 98.7%.

Figure 7:
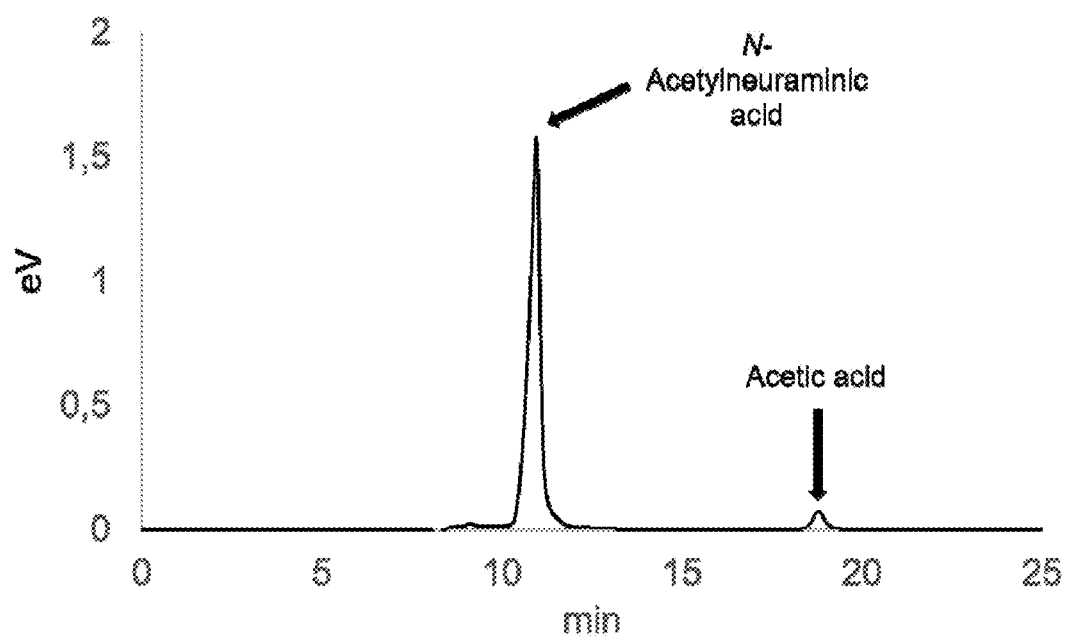

FIG. 7 shows an HPLC diagram which was recorded for N-acetylneuraminic acid that has been crystallized with acetic acid. The purity of the crystallized N-acetylneuraminic acid is detected as 98.2% in comparison to other sugars. The amount of acetic acid after drying was 2.8% in comparison to total mass of material.

Figure 8:
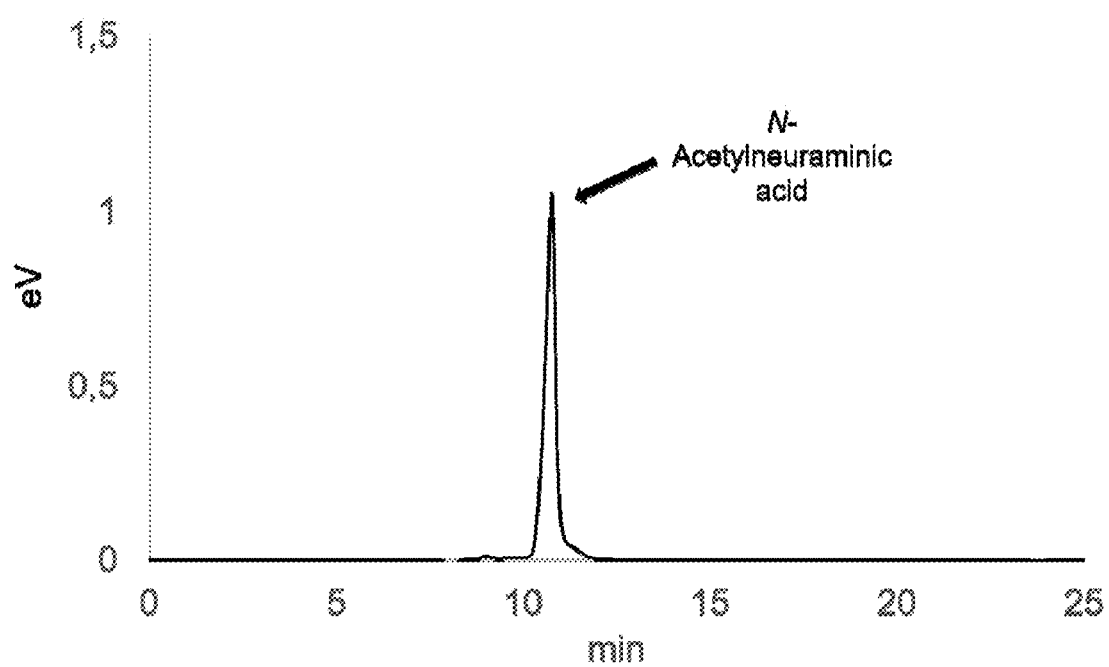

FIG. 8 shows an HPLC diagram which was recorded for N-acetylneuraminic acid that has been spray-dried. The purity of the spray-dried N-acetylneuraminic acid is detected as 99.1%.

Example 1: Purification of the Sialic Acid N-Acetylneuraminic Acid from Bacterial Fermentation The sialic acid N-acetylneuraminic acid was produced by a bacterial fermentation and harvested by filtration wherein a clear particle-free sialic acid solution (37 g/l) was obtained.

The clear particle-free solution was firstly treated with a strong cationic ion exchanger (Lewatit 52568 in proton form, Lanxess).

After neutralization with sodium hydroxide (NaOH), the solution was additionally processed with a strong anionic ion exchanger (Lewatit S 6368A in chloride form).

For concentration and desalting of N-acetylneuraminic acid in the solution after ionic exchanger treatment, the solution was further processed by a nanofiltration step. An Emrich EMRO 1.8 reverse osmosis system (Emrich Edelstahlbau) was equipped with a Trisep® XN 45 nano filtration module. The inlet pressure was set to 30 bar and the solution was concentrated until the flow rate drops under 100 liter per hour. The solution was diafiltrated three times with an equal amount of reverse osmosis water. To reduce the amount of salt, the solution was diafiltrated three times with equal volume of reverse osmosis water.

For removal of color, the N-acetylneuraminic acid containing solution was treated with activated carbon powder. The solution was incubated for 2 hours under stirring with Norit SA2 activated charcoal. After incubation the activated carbon was removed by filtration and the pH was adjusted to pH 7.0 with sodium hydroxide.

To remove remaining color and unspecific ions the solution was treated again with a strong cationic ion exchanger (Lewatit 52568 in sodium form, Lanxess) and a strong anionic ion exchanger (Lewatit S 6368A in chloride form). After said treatments, the pH was adjusted to pH 7.0.

For removal of sodium chloride, the solution was electrodialysed using a PCCell P15 electrodialysis system (PCell, Heusweiler, Germany) equipped with an PCCell ED 1000A membrane stack. Said stack comprised the following membranes: cation exchange membrane CEM:PC SK and the anion exchange membrane CEM:PcAcid60 having a size exclusion limit of 60 Da. The solution was electrodialysed until a stable conductivity was reached. During electrodialysis, the pH was stabilized at pH 7.0 by addition of NaOH.

After electrodialysis, the solution was concentrated to 20% (w/v) dry matter by reverse osmosis using an Emrich EMRO 1.8 reverse osmosis system (Emrich Edelstahlbau) which was equipped with a CSM RE8040BE reverse osmosis module.

Subsequently, the solution was filtrated to remove endotoxins and sterile filtration by passing the solution through a 5 kDa ultrafiltration membrane (Spira-Cell WY UP005 2440 C module). The sterile solution was then stored at room temperature (20° C.) and used as a sterile liquid concentrate product or the sterile solution was spray-dried.

Example 2: Conversion of the Sodium Salt of the Sialic Acid N-Acetylneuraminic Acid to its Free Acid To isolate the sialic acid in its free acid form, 30% hydrochloric acid was added after the activated charcoal treatment mentioned in Example 1 until the pH was between 1.7 and 2.3.

After the pH adjustment, the solution was treated again with a strong cationic exchanger (Lewatit 52568 in proton form, Lanxess). After ionic exchanger treatment, the solution was electrodialysed again using a PCCell P15 electrodialysis system (PCell, Heusweiler, Germany) equipped with an PCCell ED 1000A membrane stack. Said stack comprised the following membranes: cation exchange membrane CEM:PC SK and the anion exchange membrane CEM:PcAcid60 having a size exclusion limit of 60 Da. The solution was electrodialysed until a stable conductivity was reached. During electrodialysis the pH was stabilized at pH 2.0 by addition of hydrochloric acid.

Example 3: Obtaining the Sialic Acid N-Acetylneuraminic Acid in Solid Form by Spray Drying The sialic acid obtained by isolation process in sodium form or in free acid form as mentioned above in Examples 1 and 2 was concentrated to 20% (w/w) and the solution was filtrated to remove endotoxins and sterile filtration by passing the solution through a 5 kDa ultrafiltration membrane (Spira-Cell WY UP005 2440 C module, Microdyn Nadir, Wiesbaden, Germany). The so obtained sterile solution comprising N-acetylneuraminic acid was then spray-dried using a NUBILOSA LTC-GMP spray-dryer (NUBILOSA, Konstanz, Germany). For the spray-drying of the N-acetylneuraminic acid solution, the solution was passed under pressure with 3.5 bar through the spray-dryer nozzles set to 130'C and flow was adjusted to maintain an exhaust temperature between 66° C. to 67° C. Using these settings, a spray-dried powder with less than 5% moisture could be obtained. The moisture contents were determined by Karl-Fischer titration.

Example 4: Crystallization of the Sialic Acid N-Acetylneuraminic Acid as Dihydrate Form The sialic acid N-acetylneuraminic acid in free acid form was concentrated to 20% (w/w) dry matter by reverse osmosis using an Emrich EMRO 1.8 reverse osmosis system (Emrich Edelstahlbau) which was equipped with a CSM RE8040BE reverse osmosis module.

For crystallization, 5 liters of this solution was concentrated by a Hei-VAP industrial evaporator (Heidolph Instruments GmbH, Schwabach Germany) to 50% (w/w) dry matter. The solution was inoculated with seed crystals and concentrated under vacuum until crystals were formed (Dry mater of the solution: ~75% w/w).

The crystal solution was mixed 1:1 with isopropanol and stirred for 5 min. The solution was incubated for at least 12 hours at 4° C. Crystallized sialic acid was removed from the mother liquor by vacuum filtration and the crystals were washed with isopropanol.

The yield of precipitated N-acetylneuraminic acid was between 75 and 85%.

Example 5: Crystallization of the Sialic Acid N-Acetylneuraminic Acid with Acetic Acid The sialic acid N-acetylneuraminic acid in free acid form was concentrated to 30% (w/w) dry matter by reverse osmosis using an Emrich EMRO 1.8 reverse osmosis system (Emrich Edelstahlbau) which was equipped with a CSM RE8040BE reverse osmosis module.

For crystallization, 5 Liter of glacial acetic acid was added under stirring in portions to 1 liter of the N-acetylneuraminic solution. The solution was cooled down from room temperature (20° C.) to 4° C. in 3 hours. After the final temperature (4.5° C.) was reached the crystallization approach was incubated for 12 to 36 hours at this temperature.

The crystal solution was mixed 1:1 with isopropanol and stirred for 5 min. The crystallized N-acetylneuraminic acid was removed from the mother liquor by vacuum filtration and the crystals were washed twice with the equal amount of isopropanol.

The yield of precipitated N-acetylneuraminic acid was between 74 and 81%.

The purity degree in an exemplary purification of N-acetylneuraminic acid from culture broth is shown in Table 1.

TABLE 1

Purity is given as the desired mass of N-acetylneuraminic acid in comparison to the total mass.

| Purification step | Concentration sialic acid (g/l) | sialic acid (kg) | Dry Matter (kg) | Purity (%) |
|---|---|---|---|---|
| Harvest | 37 | 259 | 399 | 64.9 |
| Cationic exchanger | 37 | 256 | 382 | 67.02 |
| Anionic exchanger | 36 | 248 | 378 | 65.5 |
| Concentration/ Diafiltration | 152 | 244 | 316.6 | 77.06 |
| Activated carbon | 145 | 232.3 | 298.4 | 77.9 |

TABLE 1-continued

Purity is given as the desired mass of N-acetylneuraminic acid in comparison to the total mass.

| Purification step | Concentration sialic acid (g/l) | sialic acid (kg) | Dry Matter (kg) | Purity (%) |
|---|---|---|---|---|
| Electrodialysis | 135 | 181 | 184 | 98.3 |
| Concentration | 203 | 180 | 183 | 98.3 |

Example 6: Composition of a Representative Infant Formula Product

In the following, a composition of a representative infant formula product is presented (see Table 2 below).

The composition comprises the sialic acid Neu5Ac in combination with the abundant neutral HMOs 2'-fucosyllactose (2'-FL), 3-fucosyllactose (3-FL), lacto-N-tetraose (LNT) and optionally lacto-N-neotetraose (LNnT) and lacto-N-fucopentaose I (LNFP-I), acidic HMOs (6'-sialyllactose (6'-SL) and 3'-sialyllactose (3'-SL)), and L-fucose.

One or more probiotic strains can be present in the product. The final concentration of each ingredient is based on a preparation of 13.5 g of the powder in 90 ml of water.

TABLE 2

| | | per 100 g powder | per 100 ml infant formula |
|---|---|---|---|
| Energy | kJ | 2094-2145 | 283 |
| | kcal | 500-512 | 67-68 |
| Fats, hereof: | g | 24.2-26.2 | 3.3-3.5 |
| saturated fatty acids | g | 8.7-9.4 | 1.2-1.3 |
| monounsaturated fatty acids | g | 10.4 | 1.4 |
| polyunsaturated fatty acids | g | 5.5-5.9 | 0.7-0.8 |
| Carbohydrates | g | 56-58 | 7.4-7.9 |
| Sugars hereof: | g | 44-56 | 6-7.4 |
| Lactose | g | 44-56 | 6-7.4 |
| Sialic acid (Neu5Ac) | mg | 300-450 | 40-60 |
| L-fucose | mg | 300-450 | 40-60 |
| HMOs Hereof | g | 4.22-4.81 | 0.57-0.65 |
| 2'-FL | g | 1.85-2.22 | 0.25-0.30 |
| 3-FL | mg | 555.56-592.6 | 75-80 |
| LNT | g | 1.11 | 0.15 |
| LNnT | mg | 0-111.11 | 0-15 |
| LNFP-I | mg | 0-740.74 | 0-100 |
| 3'-SL | mg | 148.15-170.37 | 20-23 |
| 6'-SL | mg | 207.4-222.22 | 28-30 |
| Protein | g | 11.11-11.85 | 1.5-1.6 |
| Salt | g | 0.47-0.59 | 0.06-0.08 |
| Vitamins | | | |
| Vitamin A | µg | 357-358 | 47.3-48.2 |
| Vitamin D | µg | 7.8 | 1.05 |
| Vitamin E | mg | 8.15 | 1.1 |
| Vitamin K | µg | 43.7-44.4 | 5.9-6.0 |
| Vitamin C | mg | 115-118 | 15-16 |
| Vitamin B1 | mg | 0.51-0.60 | 0.068-0.079 |
| Vitamin B2 | mg | 1.3-1.7 | 0.18-0.23 |
| Niacin | mg | 3.63 | 0.49 |
| Vitamin B6 | µg | 526-600 | 71-81 |
| Folic acid | µg | 160-164 | 21.6-21.7 |
| Vitamin B12 | µg | 1.7-1.9 | 0.23-0.25 |
| Biotin | µg | 22-30 | 3.0-3.9 |
| Panthothenic acid | mg | 4.6-5.4 | 0.62-0.72 |
| Minerals | | | |
| Sodium | mg | 187-236 | 25.3-31.2 |
| Potassium | mg | 673-675 | 88.8-91.2 |
| Chloride | mg | 327-333 | 43.1-44.9 |
| Calcium | mg | 460-504 | 62.1-66.5 |

TABLE 2-continued

|  |  | per 100 g powder | per 100 ml infant formula |
|---|---|---|---|
| Phosphorous | mg | 335-352 | 45.2-46.5 |
| Magnesium | mg | 49.3-56.3 | 6.66-7.43 |
| Iron | mg | 4.15 | 0.56 |
| Zinc | mg | 3.7-3.8 | 0.49-0.51 |
| Copper | μg | 274 | 37 |
| Manganese | μg | 96.3 | 13 |
| Fluoride | μg | 30.4-32.6 | 4.1-4.4 |
| Selenium | μg | 11.1-12.3 | 1.5-1.6 |
| Iodine | μg | 101.5-103.7 | 13.7-14 |

Example 7: Composition of a Representative Premix for an Infant Formula Product Comprising Human Milk Oligosaccharides, the Monosaccharide Neu5Ac and the Monosaccharide L-Fucose In the following, a composition of a representative premix for an infant formula product is presented (see Table 3 below).

The composition comprises the sialic acid Neu5Ac in combination with the abundant neutral HMOs 2'-fucosyllactose (2'-FL), 3-fucosyllactose (3-FL), lacto-N-tetraose (LNT) and optionally lacto-N-neotetraose (LNnT) and lacto-N-fucopentaose I (LNFP-I), acidic HMOs (6'-sialyllactose (6'-SL) and 3'-sialyllactose (3'-SL)), as well as the monosaccharide free L-fucose.

The premix can be used to reconstitute an infant formula by adding said premix to other nutritional products which are necessary to reconstitute an infant food formula, such as whey, lactose, lipids (saturated and unsaturated fatty acids) and minerals. The premix shown in Table 3 is intended to be used for 1 kg of final infant formula product.

TABLE 3

| HMO/Sialic acid/Fucose Vitamin premix | | |
|---|---|---|
| Sialic acid (Neu5Ac) | g | 3.0 |
| L-fucose | g | 3.0 |
| 2'-FL | g | 18.5 |
| 3-FL | g | 5.5 |
| L/VT | g | 10.0 |
| 3'-SL | g | 1.5 |
| 6'-SL | g | 2.0 |
| Vitamins | | |
| Vitamin A | mg | 3.5 |
| Vitamin D | μg | 78.0 |
| Vitamin E | mg | 81.5 |
| Vitamin K | μg | 437.0 |
| Vitamin C | g | 1.1 |
| Vitamin B1 | mg | 5.1 |
| Vitamin B2 | mg | 13.0 |
| Niacin | mg | 36.3 |
| Vitamin B6 | mg | 5.2 |
| Folic acid | mg | 1.6 |
| Vitamin B12 | μg | 17.0 |
| Biotin | μg | 220.0 |
| Panthothenic acid | mg | 46.0 |

The invention claimed is:

1. A process for purification of a sialic acid from a fermentation broth, comprising:

removing biomass from a fermentation broth comprising a sialic acid, wherein a clarified solution is provided, providing a purified solution by subjecting the clarified solution to
  a cationic ion exchanger treatment with a cationic ion exchanger material, wherein the cationic ion exchanger treatment is performed under conditions in which the sialic acid passes the cationic ion exchanger material and is present in the flowthrough; and
  an anionic ion exchanger treatment with an anionic ion exchange material, wherein the anionic ion exchanger treatment is performed under conditions in which the sialic acid passes the anionic ion exchanger material and is present in the flowthrough; and
  removing salt from the purified solution by electrodialysis.

2. The process according to claim 1, wherein the process does not comprise
  i) a chromatographic separation; and/or
  ii) a use of ethanol and/or ethyl acetate; and/or
  iii) a step of eluting the sialic acid from a stationary phase with a solution comprising an organic solvent; and/or
  iv) a use of a heavy metal; and/or
  v) a step of heating the fermentation broth, the clarified solution and/or purified solution to a temperature of more than 45° C.

3. The process according to claim 1, wherein the biomass is removed from the fermentation broth by centrifugation and/or filtration.

4. The process according to claim 1, wherein in the cationic ion exchanger treatment, a strong cationic ion exchanger is used and/or in the anionic ion exchanger treatment, a strong anionic exchanger is used.

5. The process according to claim 1, wherein the cationic ion exchanger treatment is performed to remove unspecific cations and replace them by specific cation H+ or Na+.

6. The process according to claim 1, wherein the anionic exchanger step is performed to remove unspecific anions and replace them specific anion Cl− or OH−.

7. The process according to claim 1, wherein conditions under which the sialic acid passes the anionic exchanger material and cationic exchanger material are established by adjusting the pH and/or salt concentration of the clarified solution.

8. The process according to claim 1, wherein after the cationic ion exchanger treatment and the anionic ion exchanger treatment, the purified solution comprises the sialic acid, one or more colour-giving substances and salt.

9. The process according to claim 1, wherein in the anionic ion exchanger treatment, an anionic exchanger material in the chloride form is used and/or in the cationic ion exchanger treatment, a cationic ion exchanger material in the hydrogen form is used.

10. The process according to claim 1, wherein the clarified solution is subjected firstly to the cationic ion exchanger treatment and subsequently to the anionic ion exchanger treatment.

11. The process according to claim 1, wherein the purified solution is concentrated.

12. The process according to claim 1, wherein clarified solution and/or purified solution is concentrated
  i) up to a concentration of ≥100 g/L of the sialic acid; and/or
  ii) by nanofiltration at a temperature of <80° C., optionally <50° C., optionally 4° C. to 45° C., optionally 10° C. to 40° C., optionally 15 to 30° C., optionally 15 to 20° C.; and/or iii) by reverse osmosis at a temperature of 20° C. to 50° C., optionally 30° C. to 45° C., optionally 35° C. to 45° C.; and/or iv) at a pressure between >5 bar and <50 bar, optionally at a pressure between >10 bar and <40 bar, optionally at a pressure between >15 and <30 bar.

13. The process according to claim 1, wherein the electrodialysis is an electrodialysis under neutral conditions or an electrodialysis under acidic conditions.

14. The process according to claim 1, wherein after removing salt from the purified solution,
   i) the amount of salt in the purified solution is <10% (w/w), optionally <5% (w/w), optionally <1% (w/w); and/or
   ii) the conductivity is between 0.2 and 10.0 mS/cm$^2$, optionally between 0.4 and 5.0 mS/cm$^2$, optionally between 0.5 and 1.0 mS/cm$^2$.

15. The process according to claim 1, wherein the clarified solution and/or purified solution is subjected to discolouring by a treatment with activated charcoal.

16. The process according to claim 1, wherein the sialic acid comprised in the clarified solution and/or purified solution is converted into sodium form.

17. The process according to claim 1, wherein the purified solution is spray-dried.

18. The process according to claim 1, wherein the purified solution is subjected to crystallisation.

19. The process according to claim 2, wherein the process does not comprise a use of ethanol and/or ethyl acetate, and does not comprise the use of an organic solvent.

20. The process according to claim 5, wherein if the unspecific cations are replaced by H+, the pH of the flowthrough is adjusted to a pH of 6 to 8 before performing a further treatment.

21. The process according to claim 20, wherein the pH of the flowthrough is adjusted by addition of NaOH to the flowthrough.

22. The process according to claim 6, wherein if the unspecific anions are replaced by Cl−, the pH of the flowthrough is adjusted to a pH of 6 to 8 before performing a further treatment.

23. The process according to claim 22, wherein the pH of the flowthrough is adjusted by addition of NaOH to the flowthrough.

24. The process according to claim 7, wherein the pH of the clarified solution is adjusted to a pH in the range of 6 to 8.

25. The process according to claim 8, wherein the salt is NaCl.

26. The process according to claim 11, wherein the purified solution is concentrated by nanofiltration and/or reverse osmosis.

27. The process according to claim 26, wherein the purified solution is concentrated by nanofiltration, and wherein a nanofiltration membrane is used which has a molecular weight cut-off in a range of 100 to 200 kDa.

28. The process according to claim 12, wherein clarified solution and/or purified solution is concentrated up to a concentration of ≥200 g/L of the sialic acid.

29. The process according to claim 28, wherein clarified solution and/or purified solution is concentrated up to a concentration of ≥300 g/L of the sialic acid.

30. The process according to claim 15, wherein the discolouring is performed
   i) before or after a step of diafiltration and/or concentration of the clarified solution; and/or
   ii) before or after a step of electrodialysis and/or diafiltration of the clarified solution.

31. The process according to claim 16, wherein the sialic acid comprised in the clarified solution and/or purified solution is converted into sodium form by treating the purified solution with a strong cationic ion exchanger material in the sodium form.

32. The process according to claim 17, wherein the purified solution comprises the sialic acid in the sodium form.

33. The process according to claim 18, wherein the purified solution is subjected to crystallization by addition of acetic acid to the purified solution.

34. The process according to claim 33, wherein sialic acid is provided in dihydrate crystal form.

* * * * *